(12) United States Patent
Sharratt

(10) Patent No.: US 6,315,718 B1
(45) Date of Patent: Nov. 13, 2001

(54) METHOD FOR HIP RETRACTION

(75) Inventor: Todd W. Sharratt, Cottage Grove, MN (US)

(73) Assignee: Minnesota Scientific, Inc., St. Paul, MN (US)

( * ) Notice: Subject to any disclaimer, the term of this patent is extended or adjusted under 35 U.S.C. 154(b) by 0 days.

(21) Appl. No.: 09/654,400

(22) Filed: Sep. 1, 2000

Related U.S. Application Data

(60) Provisional application No. 60/157,488, filed on Oct. 4, 1999.

(51) Int. Cl.$^7$ .................................................. A61B 1/32
(52) U.S. Cl. ................................. 600/228; 600/235
(58) Field of Search .................... 600/201, 227, 600/228, 230, 235; 606/90; 128/882, 898; 602/32, 33, 34, 35, 39

(56) References Cited

U.S. PATENT DOCUMENTS

| | | |
|---|---|---|
| 3,710,783 | 1/1973 | Jascalevich . |
| 4,021,865 | 5/1977 | Charnley . |
| 4,402,481 | 9/1983 | Sasaki ................................. 248/276 |
| 4,424,724 | 1/1984 | Bookwalter et al. .................. 74/540 |
| 4,491,435 | 1/1985 | Meier ................................... 403/55 |
| 4,520,805 | 6/1985 | St. Vincent et al. . |
| 4,573,452 | 3/1986 | Greenberg . |
| 4,747,395 | 5/1988 | Brief . |
| 4,964,400 | * 10/1990 | Laico et al. . |
| 4,995,875 | * 2/1991 | Coes ................................. 600/235 X |
| 5,192,283 | 3/1993 | Ling et al. ............................. 606/63 |
| 5,303,694 | * 4/1994 | Mikhail . |
| 5,470,336 | 11/1995 | Ling et al. ............................. 606/105 |
| 5,507,824 | 4/1996 | Lennox .................................. 623/22 |
| 5,704,900 | * 1/1998 | Dobrovolny et al. ............ 600/227 X |
| 5,755,720 | 5/1998 | Mikhail ................................. 606/94 |
| 5,880,976 | 3/1999 | Digioia, III et al. ................. 364/578 |

FOREIGN PATENT DOCUMENTS

4103070-A * 8/1991 (DE) ....................................... 606/90

OTHER PUBLICATIONS

Mayo Clinic Health Letter, *Hip Replacement*, vol. 12, No. 8, Aug. 1994, pp. 1–3.

W.C. Campbell, M.D., Operative Orthopaedics, *Arthroplasty of Hip*, vol. 1, Ninth Edition, Chapter 7, 1998, pp. 296–355.

American Academy of Orthopaedic Surgeons Public Information, *Total Joint Replacement*, 1999, pp. 1–3.

J.E. Stevens, Technology Review; *Robodoc: a kinder, gentler surgeon's assistant*, May–Jun. 1996, v99, n4, p14(2).

* cited by examiner

*Primary Examiner*—Jeffrey A. Smith
(74) *Attorney, Agent, or Firm*—Kinney & Lange, P.A.

(57) ABSTRACT

A method for performing hip surgery using at least one support arm attached to a retractor support apparatus. The surgery includes incising the patient so as to expose the hip joint including the femoral head, the acetabulum and a portion of the femur. A femur retractor is positioned on the support arm and engages the femur, thereby dislocating the femoral head from the acetabulum. After disengaging the femur retractor from the femur, a femur elevating retractor is positioned on the support arm. The femur elevating retractor elevates the femoral head, thereby creating access to the acetabulum.

57 Claims, 12 Drawing Sheets

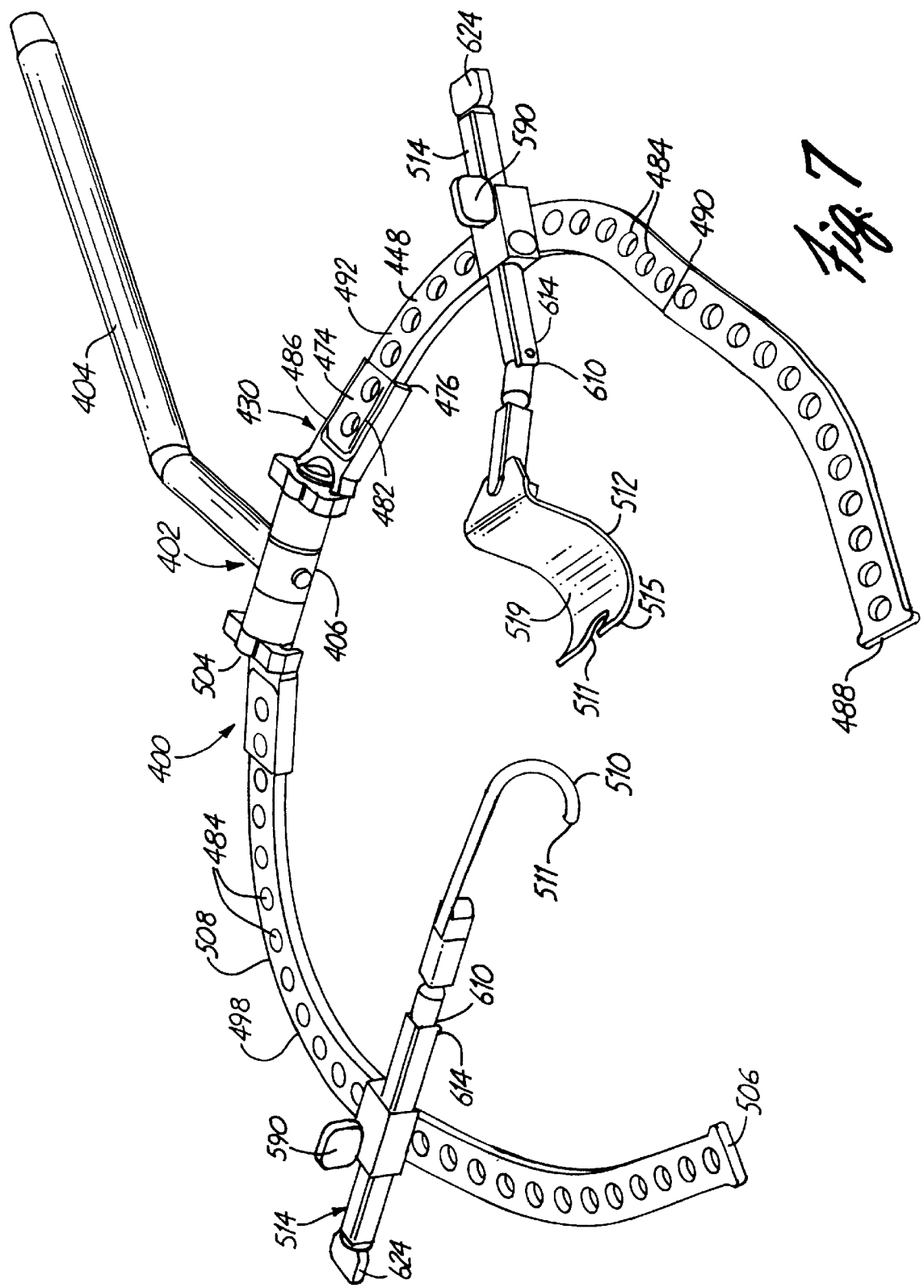

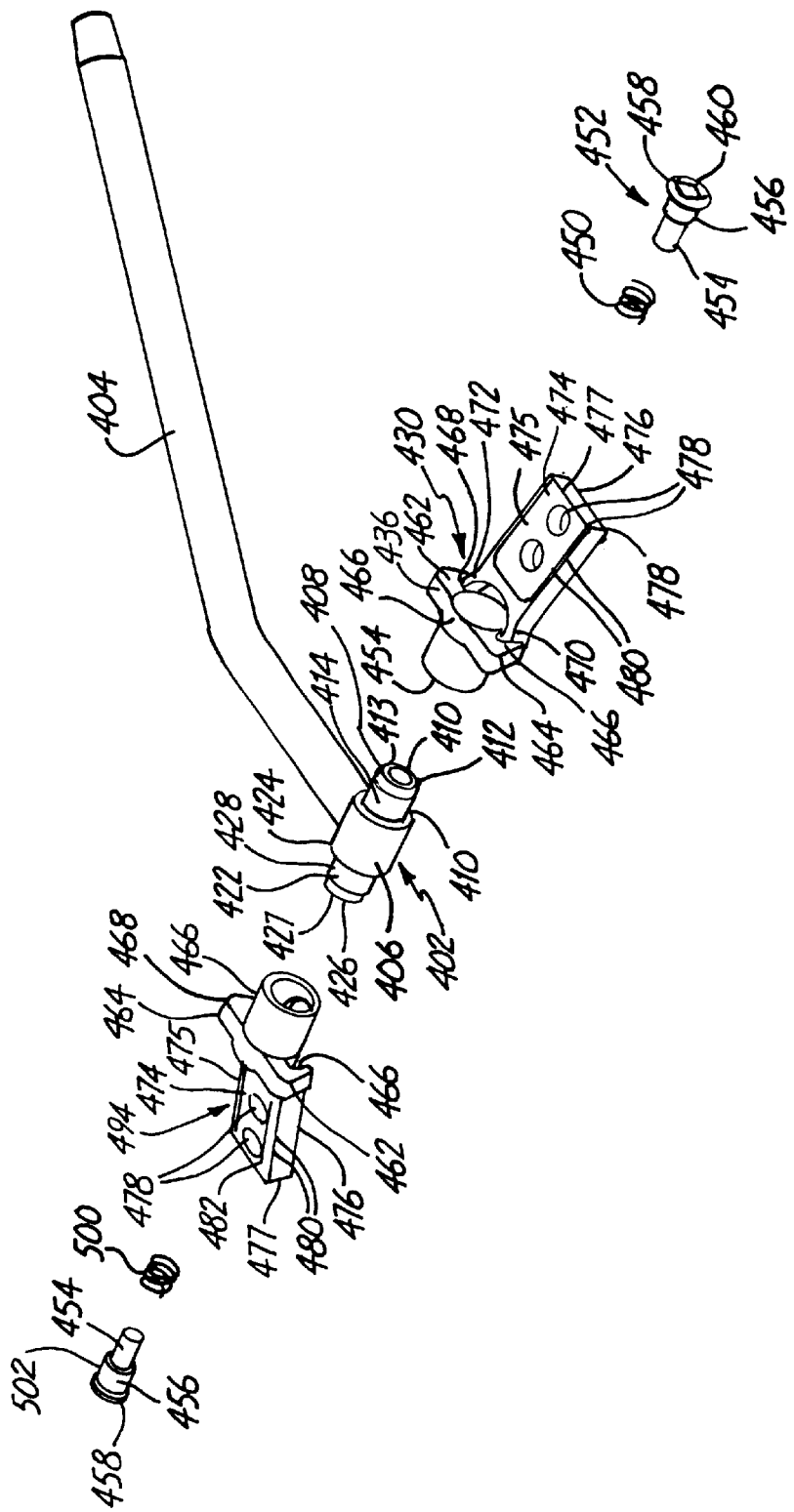

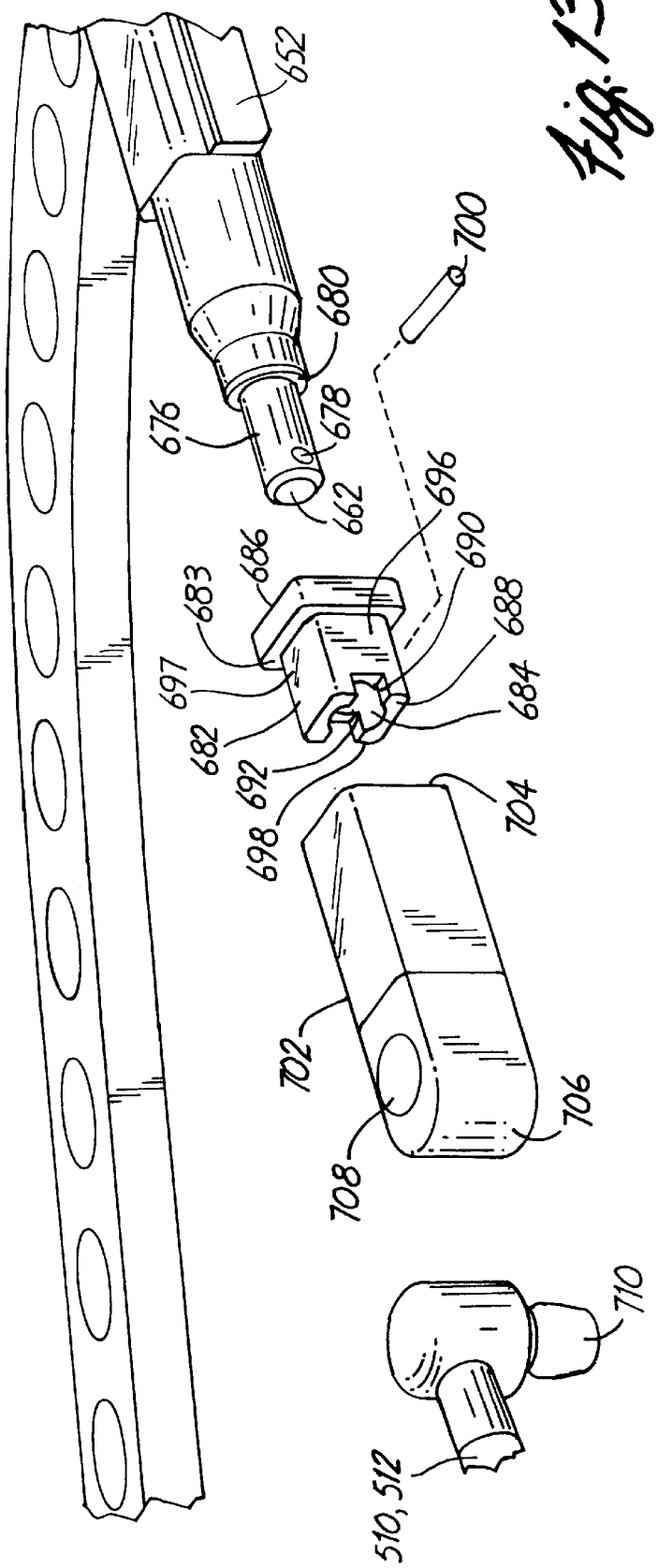

METHOD FOR HIP RETRACTION

CROSS-REFERENCE TO RELATED APPLICATION

Applicant claims the priority date of U.S. Provisional Application 60/157,488, filed Oct. 4, 1999.

BACKGROUND OF THE INVENTION

The present invention relates to surgical retractor apparatus. In particular, the present invention relates to a retractor apparatus that is attached to a retractor mounting apparatus.

Total hip replacement (arthroplasty) operations have been performed since the early 1960's to repair hip components. These components include the acetabulum (socket portion of the hip) and the femoral head (ball portion of the hip). The hip is typically replaced due to a gradual deterioration of the cartilage that cushions the bones within the joint. The surrounding structures in the hip begin to grow irregularly and can become inflamed and painful. Eventually, bone can begin to rub against bone causing severe discomfort.

Surgical procedures have been the most successful method to alleviate this pain. Either partial or total hip replacement surgery can be used. In total hip replacement, a cup shaped insert typically manufactured of polyethylene is inserted in place of the acetabulum, and a metal femoral head is placed in the femur. A number of variations have evolved in the surgical approaches and techniques used for replacement of the hip components, including operating while the patient is on his or her back (supine) or on his or her side (lateral). Additionally, the surgeon may perform an osteotomy of the greater trochanter portion of the femur which is reattached after insertion of the femoral insert. To a large extent, the choice of surgical approaches is due to the surgeon's preference as to what aspect of the hip components the surgeon wishes to view. The ability to view the surgical site is complicated by the need to remove the femoral head from the acetabulum as well as rotate and retract the femur in the wound during surgery.

The surgeon makes an incision along the hip and divides the tissue and muscle to expose the hip joint. The femoral head is removed from the acetabulum typically using a bone hook placed under the end of the femur proximate to the acetabulum. The femoral head is lifted out, along with flexing, adducting and internally rotating the hip. Typically, at least two strong people are needed to perform this part of the operation, since lifting and moving the leg can be a very strenuous activity that must be precisely performed. The proximal femur is then rotated upwardly into the wound using a broad flat retractor used as a lever which exposes the femoral head. The surgeon can perform the osteotomy of the femoral neck if desired. Using a retractor, the femur is retracted anteriorly and medially and rotated to provide acetabular exposure. The surgeon reams the acetabulum and places an acetabular implant into the acetabulum which is typically cemented in place.

To insert the femoral component, the proximal end of the femur is exposed. A common method to expose the femur is to rotate the femur so that the tibia is perpendicular to the floor. A broad, flat retractor is placed under the femur and the femur is levered upwards, out of the wound. The femoral component is then inserted. During this process, a pointed reamer is hammered into the femoral canal. A broach is inserted to enlarge the canal and a trial head is positioned within the canal. The hip is reduced (the femoral component is inserted into the acetabulum component) to check the angle and fit of the femoral head insert into the acetabulum insert. If the hip components do not adequately fit, the hip is again dislocated, the components adjusted, and the hip reducted. If the stability and placement of the trial inserts is acceptable, the hip is dislocated and the femoral implant stem is placed into the medullary canal of the femur. The hip is again reduced and the stability of the arthroplasty is confirmed. If the stability is questionable, the hip may again be dislocated, the components adjusted, and the hip reducted.

Due to the multiple dislocations and reductions, as well as retracting and rotating the femur, the surgical procedure can become quite physically taxing on the surgeon or surgeons performing it. The surgical procedure requires lifting and moving the patient's femur into multiple positions. At times, the surgeon may need to hold the femur in position for an extended period of time. Depending on the size of the patient, the strenuous activity can lead to fatigue and contribute to surgical error. Additionally, the repeated movement of the leg can cause nerve damage if it is not done precisely and with minimal adjustment. When the surgeon moves the femur by hand it is common to have continual adjusting occur. Often, the surgeon holding the leg, relaxes or becomes fatigued and allows the leg to move, requiring that the leg be readjusted. The movement can cause the leg to pinch tor rub nerves or muscle tissue, possibly causing damage.

BRIEF SUMMARY OF THE INVENTION

The present invention is a method for dislocating, retracting and manipulating the femur bone when performing hip surgery. At least one support arm is attached to a retractor mounting apparatus. The surgical procedure includes incising a patient so as to expose the hip joint which includes the femoral head, the acetabulum and a portion of the femur. A femur retractor is positioned on one of the support arms and engages the femur thereby dislocating the femoral head from the acetabulum. After disengaging the femur retractor from the femur, a femur elevating retractor is positioned on the support arm. The femur elevating retractor engages the femur and elevates the femoral head from the acetabulum which creates access to the acetabulum.

BRIEF DESCRIPTION OF THE DRAWINGS

FIG. 7 is a perspective view of a retractor apparatus mounted embodiment of the present invention.

FIG. 8 is an exploded perspective view of a cross arm assembly of the retractor apparatus mounted embodiment of the present invention.

FIG. 13 is an exploded perspective view of a retractor engaging end of a retractor mechanism of the present invention.

DETAILED DESCRIPTION

Figure 1:
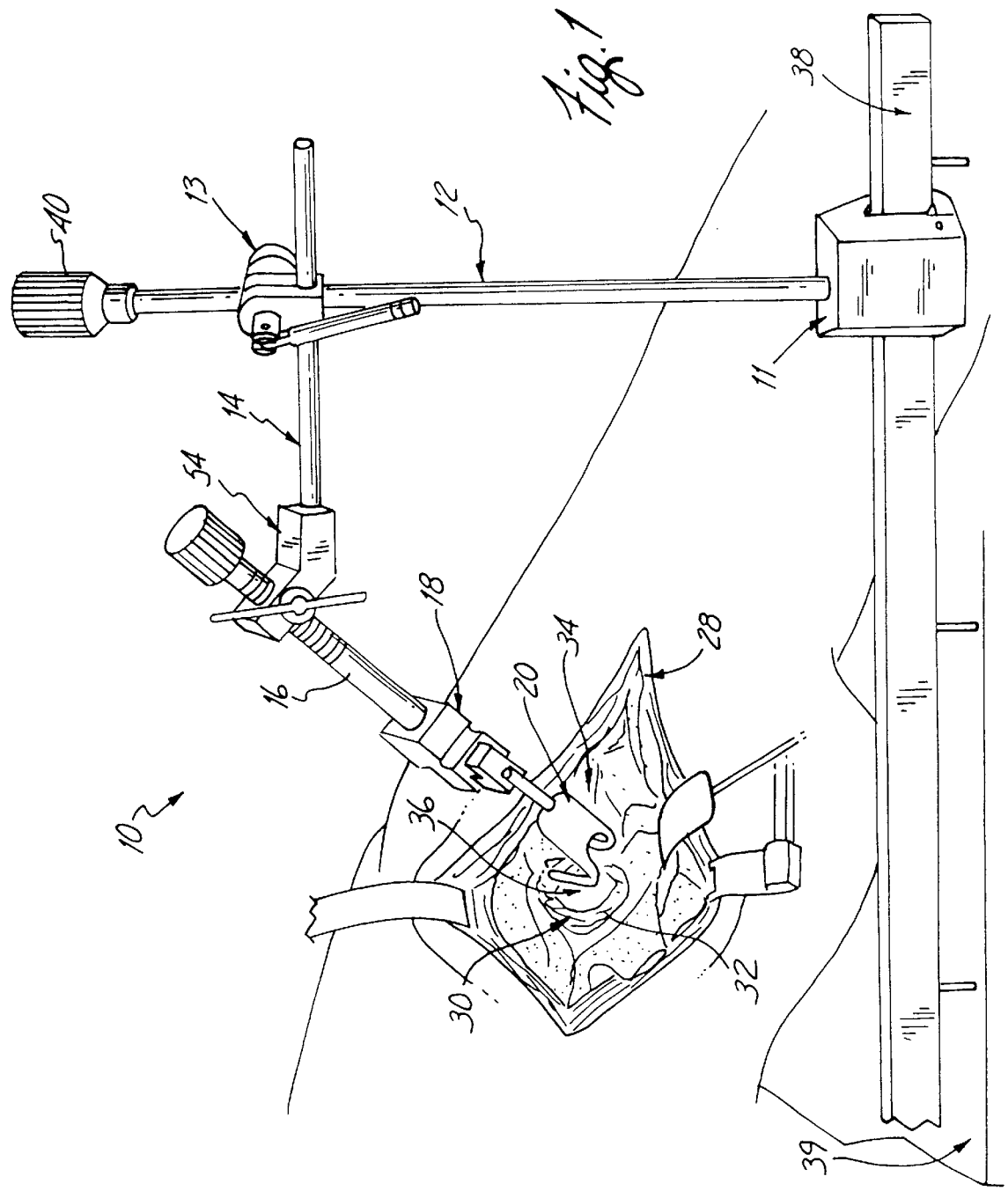
FIG. 1 is a perspective view of a table mounted embodiment of an inventive retractor assembly of the present invention.

A table mounted hip retractor assembly is illustrated generally at 10 in FIG. 1. The retractor assembly 10 includes a sidebar clamp 11, a support post 12, a support clamp 13, a support arm 14, a retractor arm 16, an articulated joint assembly 18, and a blade 20.

An incision 28 over an exposed hip joint 30 is illustrated in FIG. 1. The hip joint 30 includes acetabulum 32, femur 34, and femoral head 36. The blade 20 grips the femoral head 36, allowing the manipulation of the femoral head 36 with respect to the acetabulum 32.

The retractor assembly 10 is mounted to a table sidebar 38, and the table sidebar 38 is in turn mounted to an operating table 39. Using the table sidebar 38 to mount the retractor assembly 10 allows a surgeon to use the operating table 39 to provide a stable counter-force when retracting and manipulating the femoral head 36. The retractor assembly 10 is mounted to the table sidebar 38 using the sidebar clamp 11. The sidebar clamp 11 is manufactured to allow the clamp to be alternatively fixed in position relative to the sidebar 38, or slidable relative to the sidebar 38. The preferred embodiment of the sidebar clamp 11 is best described in U.S. Pat. No. 5,400,772 herein incorporated by reference.

The support post 12 extends upwardly from the sidebar clamp 11. The length of the support post 12 must be long enough to allow the blade 20 to be extended into the hip joint 30. A grip 40 is rotatably engaged with the support post 12. Rotating the grip 40 clamps and unclamps the sidebar clamp 11.

The support clamp 13 is slidably mounted to the support post 12. The support clamp 13 can be clamped to fix the position of the clamp 13 relative to the support post 12 and the support arm 14. Alternatively, the support clamp 13 can be unclamped to allow the support post 12 and the support arm 14 to slide and rotate relative to the support clamp 13. The preferred embodiment of the support clamp 13 is best described in U.S. Pat. No. 5,400,772.

The sidebar clamp 11 and the support clamp 13 are examples of the types of clamps that may be used in one embodiment of the invention. Other retractor clamping methods are known in the art, and a person skilled in the art would realize numerous types and methods of clamping are available which do not depart from the spirit and scope of the invention.

Figure 2:
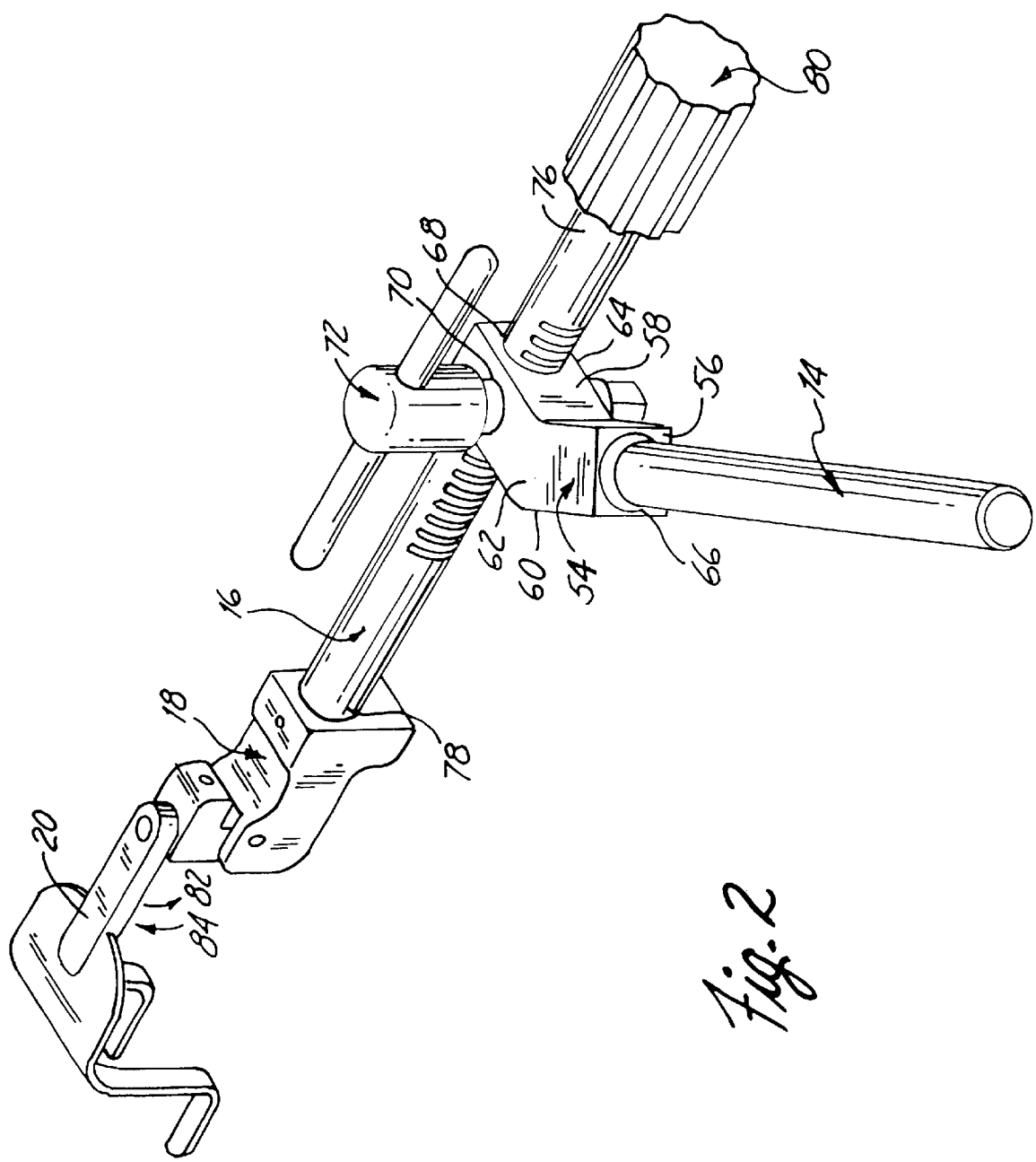
FIG. 2 is a perspective view of the table mounted embodiment of the inventive retractor assembly of the present invention.

The support arm 14 is coupled to an angle bar 54, as best illustrated in FIG. 2. The angle bar 54 is generally L shaped. The angle bar 54 includes an end face 56, a concave face 58, a convex face 60, a first side face 62 and a second side face 64. A threaded bore 66 extends into the bar 54 through the end face 56. The support arm 14 is screwed into the threaded bore 66. The first side face 62 and the second side face 64 are parallel to each other and extend in a perpendicular plane from the end face 56. The concave face 58 and convex face 60 are generally parallel to each other and extend between the first side face 62 and the second side face 64. A retractor bore 68 extends into the bar 54 through the concave face 58, through the angle bar 54 and out the convex face 60. The retractor arm 16 extends through the retractor bore 68. A gear bore 70 extends through the angle bar 54 through first and second side faces 62 and 64. A gear pin 72 extends through the gear bore 70.

The retractor arm 16 runs longitudinally from a handle end 76 to a blade end 78. The retractor arm 16 is disposed within the retractor bore 68, so that the handle end 76 is disposed more proximately to the concave face 58 and more distally from the convex face 60 of the angle bar 54 (although in other embodiments, the retractor arm 16 may extend through the retractor bore 68 in the reverse direction). Rotating the gear pin 72 moves the retractor arm 16 longitudinally through the retractor bore 68.

A turning knob 80 is fixed to the handle end of the retractor arm 16. The articulated joint assembly 18 is fixed to the blade end 78 of the retractor arm 16, and is adapted to receive the retractor blade 20. When the knob 80 is rotated in one direction, the articulated joint 18 and the attached blade end 20 hinge downward (in the direction of arrow 82). When the knob 80 is rotated in the opposite direction, the articulated joint assembly 18 and the attached blade hinge 20 upward (in the direction of arrow 84). Additionally, the articulated joint assembly 18 is annularly rotatable about the blade end 78 of the retractor arm 16. The blade 20 can thereby be disposed in a multitude of positions by the surgeon.

Figure 2A:
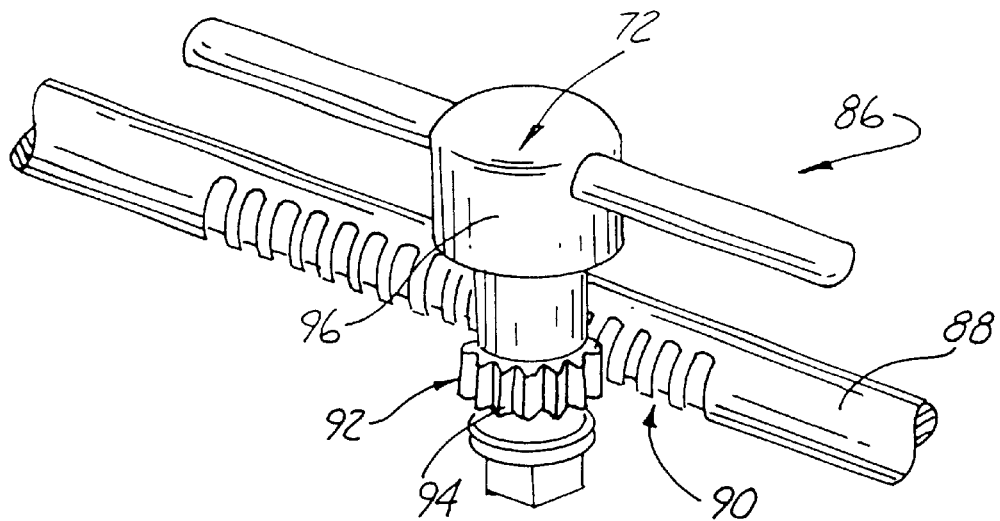
FIG. 2A is a perspective view of a rack and pinion portion of the table mounted embodiment the inventive retractor assembly of the present invention.

The retractor bore 68 and the gear bore 70 are disposed perpendicularly and tangentially with each other in the angle bar 54. Since they run tangentially, a portion of the retractor bore 68 opens into a portion of the gear bore 70. Longitudinal movement of the retractor arm 16 through the retractor bore 68 is accomplished using a rack and pinion system 86 as best illustrated in FIG. 2A. The retractor arm 16 has an outer surface 88. A rack 90 is disposed into the outer surface 88, proximate to the gear pin 72. The rack 90 extends along the outer surface 88 and determines the maximum distance the retractor arm 16 can be moved through the retractor bore 68 by the rack and pinion system 86.

A gear 92 having pinions 94 is disposed annularly around the gear pin 72. The gear 92 is disposed so that the pinions 94 will engage grooves in the rack 90 when the gear pin 72 is rotated. The gear 92 is able to engage the rack 90 because the gear bore 70 and the retractor bore 68 are in communication internal to the angle bar 54. A gear pin handle 96 is disposed on the gear pin 72 and allows the surgeon to easily grip and rotate the pin 72. Since the femoral head 36 is engaged with the blade 20, rotation of the gear pin handle 96 allows the surgeon to dislocate the femoral head 36 from the acetabulum 32 and allows the surgeon to pull on the femur with force parallel to the bone to test for proper tension prior to reduction (installation of the prostheses femur head).

Figure 3A:
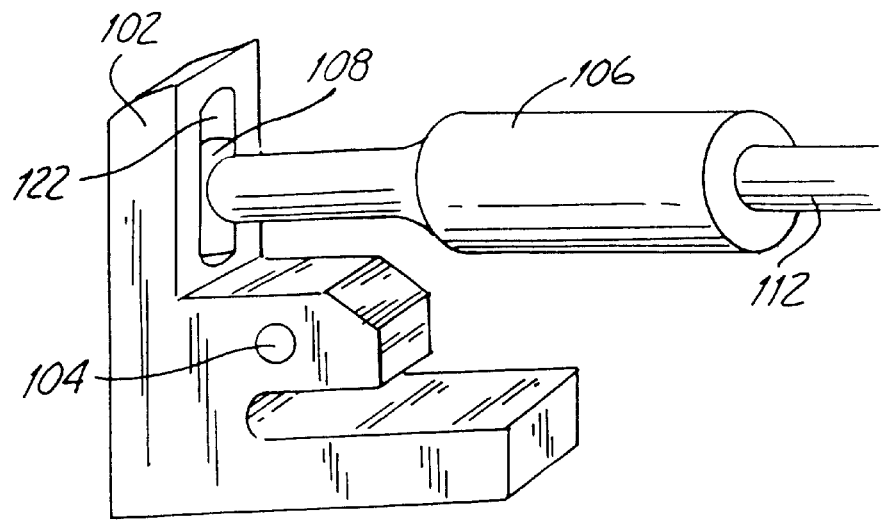
FIG. 3A is a partial perspective view of a finger and rod adapter connection in an articulated joint of the table mounted embodiment of the inventive retractor assembly.
Figure 3:
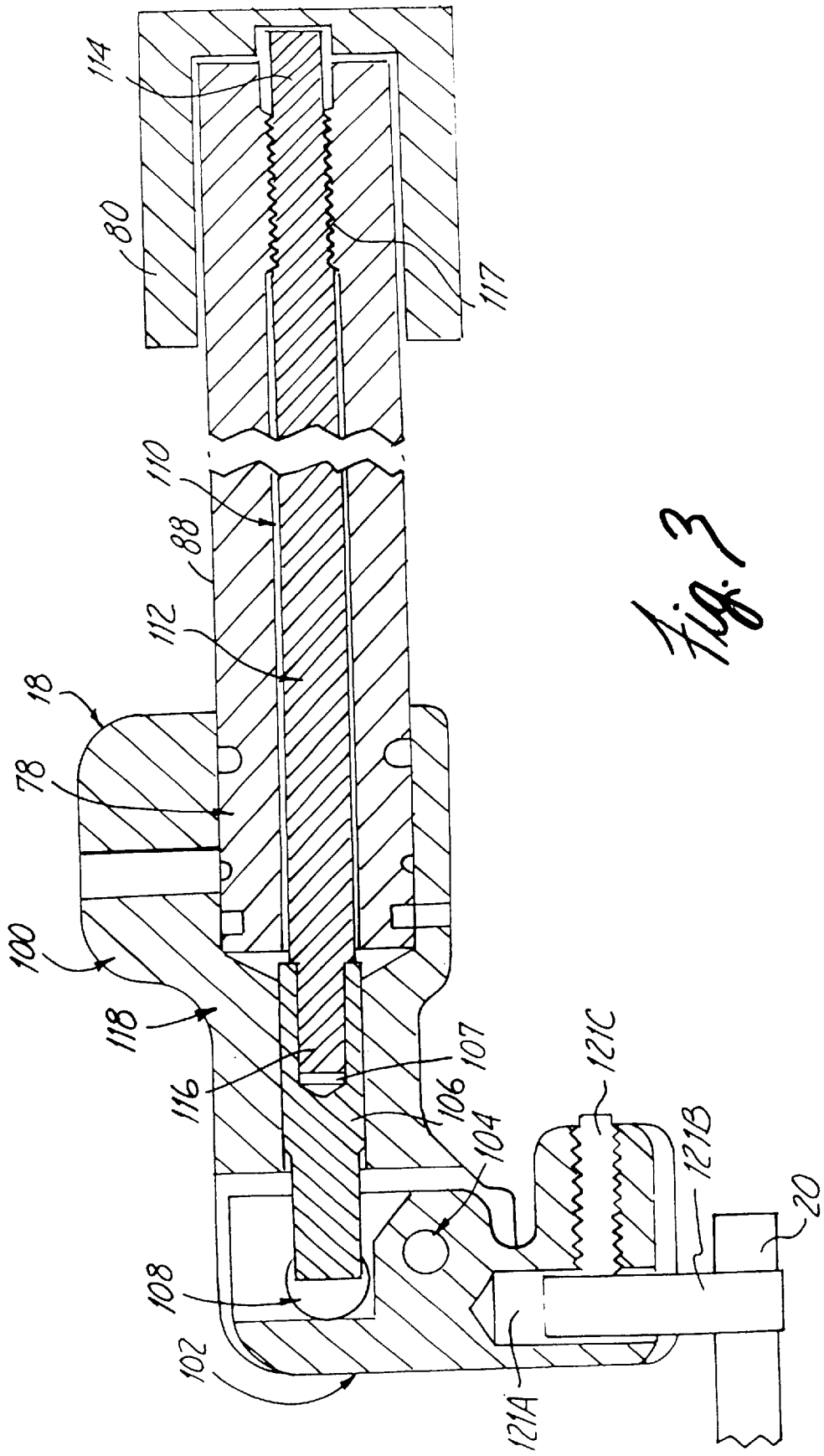
FIG. 3 is a fragmentary cross-sectional view of the table mounted embodiment of the inventive retractor assembly.

Articulation of the blade 20 is provided by the articulated joint assembly 18 as best illustrated in FIG. 3. The assembly 18 includes a main body 100, a finger 102, a pivot pin 104, a rod adaptor 106, and a ball 108. The retractor arm 16 is shaped to form a tube having an internal channel 110. A push rod 112 extends through the internal channel 110. The push rod 112 has a handle end 114 and a blade end 116. The turning knob 80 is attached to the handle end 114 of the push rod 112. The push rod 112 and the internal channel 110 engage at threaded sections 117 so when the push rod 112 is rotated in one direction, the push rod 112 is moved towards the blade end 78 of the retractor arm 16. When the push rod 112 is rotated in an opposite direction, the push rod 112 is moved towards the handle end 76 of the retractor arm 16.

The blade end 116 of the push rod 112 extends into the rod adaptor 106. Typically, the rod adaptor 106 has an internal bore 107 into which the push rod 112 is press fit. The ball 108 is mounted onto the end of the rod adaptor 106. A portion of the main body 100 encompasses the outer surface 88 of the blade end 78 of the retractor arm 16. A shoulder portion 118 of the main body 100 extends longitudinally from the blade end 78 of the retractor arm 16. The shoulder portion 118 of the main body 100 encompasses the blade end 116 of the push rod 112, and the rod adaptor 106. The finger 102 is disposed at the distal end of the shoulder portion 118. The finger is "L" shaped with a bore 121A extending into the junction point of the "L". A blade pin 121B is fixed to the blade 20, and is extended into the bore 121A of the finger 102, and secured with a screw 121C. The pivot pin 104 extends through the shoulder portion 118 and the finger 102, allowing the finger 102 to pivot with respect to the shoulder 118.

The rod adaptor 106 extends through the shoulder portion 118 so that the ball 108 engages the finger 102. When the push rod 112 is extended or retracted through the internal channel 110 of the retractor arm 16, the ball 108 acts on the finger 102 causing the finger 102 to rotate about the pivot pin 104. The ball 108 is captured inside a slot in the finger 102 as shown in FIG. 3A. Capturing the ball 108 in this fashion allows the finger 102 to be both pushed and pulled by the push rod 112. The slot 122 is necessary for the ball 108 to translate linear motion to rotational motion, since as the finger rotates, the contact point between the ball 108 and the finger 102 translates along the length of the finger 102. When the surgeon rotates the turning knob, he or she is able to pivot the femoral head 36 engaged with the blade 20.

Figure 4:
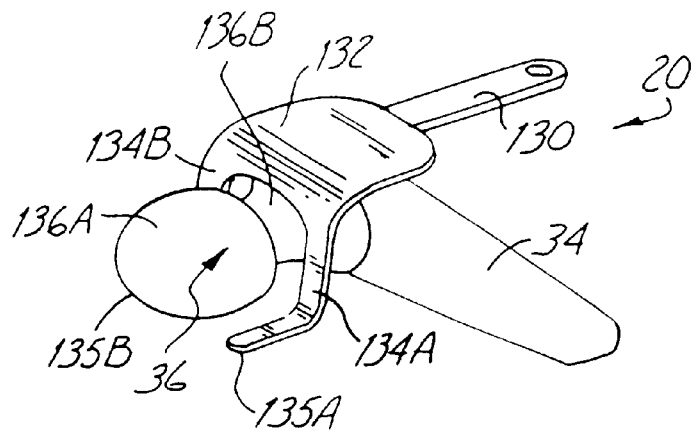
FIG. 4 is a perspective view of a blade portion of the table mounted retractor assembly engaged with a femoral head from a typical hip joint.

The blade 20 includes a stem 130, a plate section 132, a first and second prong 134A and 134B, and a first and second projection 135A and 135B, as best illustrated in FIG. 4. The stem 130 runs longitudinally and is secured into the bore 121A in the finger 102 as described above. The stem 130 is fixed to the plate portion 132 of the blade 20. The plate 132 runs substantially within the same plane as the stem 130 for a distance substantially covering the width of a typical femur 34. The distal end of the plate 132 bends perpendicularly to the plane of the stem 130. The perpendicular portion of the plate 132 is U-shaped, forming prongs 134A and 134B. The prongs 134A and 134B extend perpendicularly for approximately the distance of the width of a typical femur 34. The distal ends of the prongs 134A and 134B bend into a plane parallel with the stem 130, forming projections 135A and 135B. The projections 136A and 136B extend away from the stem portion of the blade 20.

The blade 20 is shaped to engage the femur 34 after the femoral head 36 has been dislocated from the acetabulum 32. The femoral head 36 includes a ball portion 136A and a trunk portion 136B. The surgeon places the blade 20 over the femoral head 36 so that the first and second prong 134A and 134B are disposed on opposite sides of the trunk portion 136B and between the ball 136A and femur 34. The projections 135A and 135B are placed so as to be in supportive engagement with the ball portion 136A of the femoral head 36.

Figure 5A:
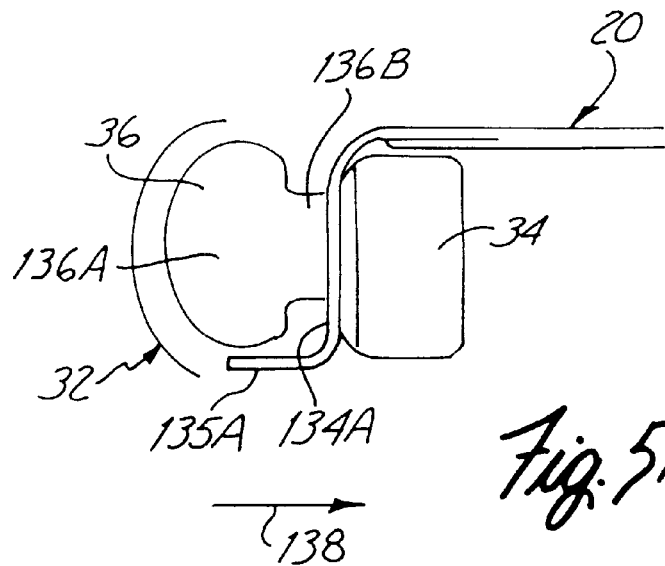
FIG. 5A is a side view of the blade portion of the table mounted retractor assembly engaging the top side of the femoral head ball.
Figure 5B:
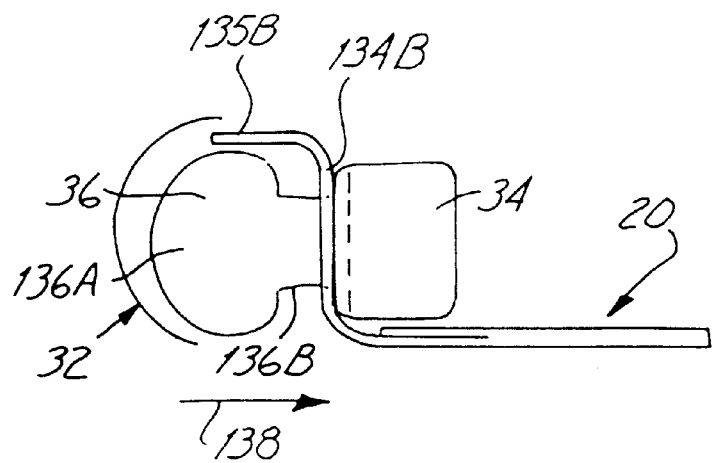
FIG. 5B is a side view of the blade portion of the table mounted retractor assembly engaging the bottom side of the femoral head ball.

The positioning of the retractor assembly 10 varies according to the view desired by the surgeon performing the operation. The multiple degrees of freedom allowed by the retractor assembly 10 allows the femur to be retracted and manipulated in a variety of directions. The general procedure, however, is the same. Typically, after the blade 20 is positioned on the femoral head 36, the gear pin handle 96 is rotated to move the retractor arm 16 through the retractor bore 68 towards the handle end 76. Since the blade end 78 of the retractor arm 16 is engaged with the femoral head 36, the blade 20 and the engaged femoral head 36 are pulled towards the handle end 76 of the retractor arm 16. This movement allows the surgeon to use a mechanical movement of the rack and pinion system 86 of the retractor assembly 10 to dislocate the femoral head 36 from the acetabulum 32, as illustrated in FIGS. 5A and 5B. The first and second prongs 134A and 134B engage the femur 34 transversely during dislocation, and pull the ball 136A away from the acetabulum 32 (in the direction of arrow 138).

Using the mechanical system provided by the retractor assembly 10 allows the hip joint to be dislocated with a minimum amount of force. The use of the inventive retractor assembly avoids the problem of requiring the surgeon or assistant to bear the full weight of the patient's leg until a supporting structure can be put in place. Physical fatigue by the surgeon is avoided decreasing the possibility of surgical error. Additionally, the rack and pinion system 86 used by the retractor assembly 10 allows the femoral head 36 to be precisely retracted. The surgeon can dislocate the head 36 as far as is minimally necessary, whereas dislocation without the mechanical structure of the inventive retractor assembly 10 can result in a less precise displacement of the femoral head 36 from the acetabulum. Displacing the femur 34 too far can unnecessarily strain the patient's leg, a problem avoided by the inventive retractor assembly 10.

Figure 6A:
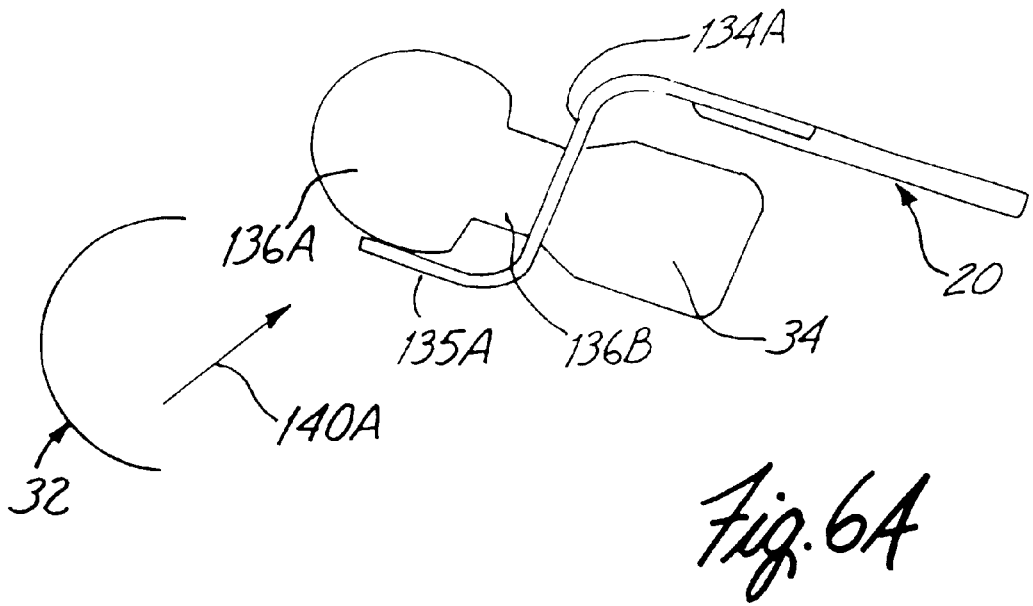
FIG. 6A is a side view of the blade portion of the table mounted retractor assembly where the femoral head is rotated upwardly.
Figure 6B:
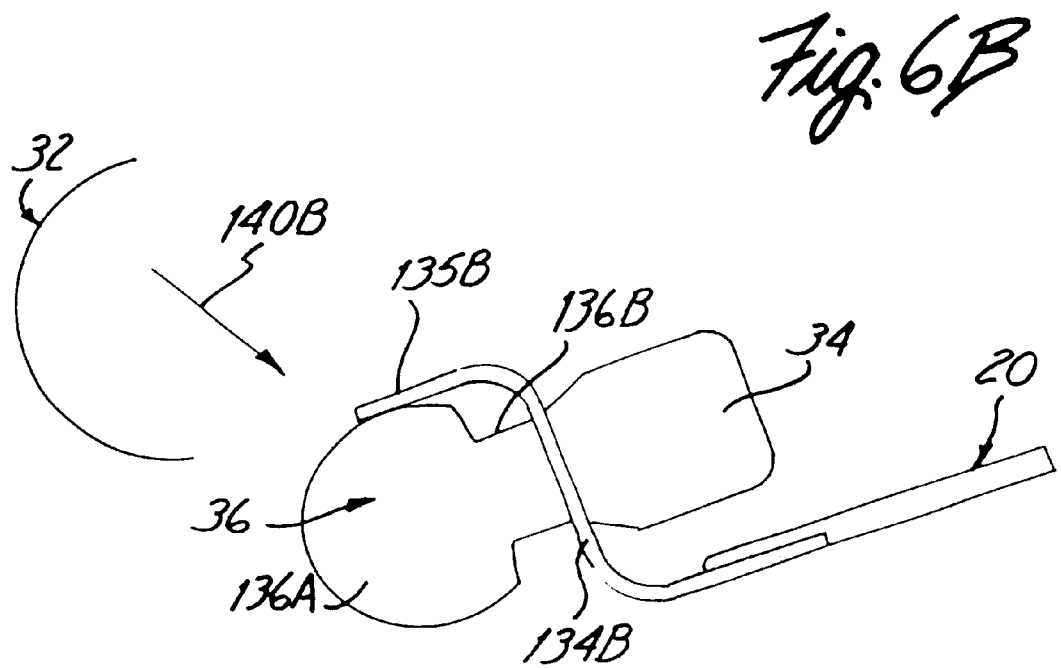
FIG. 6B is a side view of the blade portion of the table mounted retractor assembly where the femoral head is rotated downwardly.

The blade 20 can be rotated so that the first and second projections 135A and 135B extend over any portion of the ball 136A (for example, above and below the ball 136A as illustrated in FIGS. 5A and 5B). The blade 20 is positioned by rotating the main body 100 of the articulated joint assembly 18 annularly about the retractor arm 16. Rotating the blade 20 about the femoral head 36 allows the surgeon to position the blade 20 optimally to retract the femoral head 36 after dislocation from the acetabulum 32, as illustrated in FIGS. 6A and 6B. Preferably the first and second projections 135A and 135B are placed below the ball 136A when elevating the femoral head 36 and above the ball 136A when depressing the femoral head 36, however, a person skilled in the art would realize alternate positions can be used to operate the inventive retractor assembly 10.

The femoral head 36 may be elevated (arrow 140A in FIG. 6A) or depressed (arrow 140B in FIG. 6B) to provide the surgeon with a desired view of the acetabulum 32. The first and second projections 135A and 135B engage the ball 136A to transfer rotational force to the ball 136A. The blade 20 is pivoted using the articulated joint assembly 18. Again, a mechanical movement is provided by the retractor assembly 10 to precisely pivot the femoral head 36. Once retracted into the desired position, there is no errant movement of the femur 34, since the patient's leg is supported by the table mounted retractor assembly 10 and does not require additional support to immobilize the leg (although a person skilled in the art would realize that additional support may be used). Support for the leg is effectively provided by the operating table 39 and the hip retractor assembly 10. Surgeon fatigue is avoided, preventing unnecessary movement of the femoral head 36 towards and away from the acetabulum 32 as may occur when the surgeon is manually retracting the femoral head 36. Since the retractor assembly 10 is mounted to the table 39, the force required to pull the femoral head 36 from the acetabulum 32 is transferred from the supporting operating table 39, through the retractor assembly 10 to the retractor blade 20. The use of the table 39 as support can eliminate the need for as many people to be involved in the surgical procedure, since less manpower is necessary to manipulate the leg. Because fewer people are required to perform the surgery, the surgical procedure can be provided at a lower cost.

Surgical procedural variations can be easily accommodated by the hip retractor assembly 10. If the hip joint 30 needs to be reduced and dislocated multiple times to verify the fit of the replacement components, the femoral head 36 can be rotated back into alignment with the acetabulum 32 by rotating the turning knob 80 on the retractor arm 16. The hip joint 30 is reduced by rotating the gear pin handle 96 to reposition the femoral head 36 (or its replacement component) into the acetabulum 32 (or the acetabulum insert). Since repositioning of the femur 34 and femoral head 36 is performed by mechanical movement, the procedure is less labor intensive which increases the surgeon's ability to precisely position the artificial hip components.

Additionally, the support post 12 and support arm 14 can be manipulated by the surgeon to provide additional range of motion for the femoral head 36. Swinging or rotating the support arm 14, sliding the support clamp 13 up and down the support post 12, rotating the support post 12 or sliding the support clamp 13 along the sidebar 38 enables the entire retractor arm 16 to be moved in a myriad of directions which allows the surgeon to position the femoral head 36 as he or she desires and then lock it into place. Locking and unlocking the position of the femoral head 36 in this manner is accomplished by rotating the first clamp pin 42 in the sidebar clamp 11 and the second clamp pin 50 in the support clamp 13.

By supplying multiple positioning methods which can dislocate, retract and lock the positions of the femoral head 36 relative to the acetabulum 32, the retractor assembly provides an efficient, precise method for the surgeon to manipulate the femoral head 36 when performing total hip replacement surgery. The apparatus allows the surgeon to use the mechanical movement afforded by gearing mechanisms in the retractor assembly 10 as well as using the operating table to provide structural support to the femoral head 36 and femur 34 during the surgery.

An alternative embodiment is generally illustrated in FIG. 7 at 400. The alternative embodiment 400 is secured to a retractor support apparatus (not shown) instead of being directly mounted to the surgical table (not shown) although the retractor support apparatus (not shown) may be mounted to the surgical table (not shown). The alternative embodiment 400 includes a cross arm subassembly 402 having a support member 404 extending outwardly from a cylindrical portion 406. The support member 404 is of a diameter such that a clamping member well known in the art secures the cross arm subassembly 402 to a member of the retractor support apparatus (not shown).

Referring to FIG. 8, a first engaging portion 408 extends outwardly from the cylindrical portion 406. The first engaging portion 408 has a smaller diameter than the diameter of the cylindrical portion 406 thereby defining a first shoulder 410.

Figure 11:
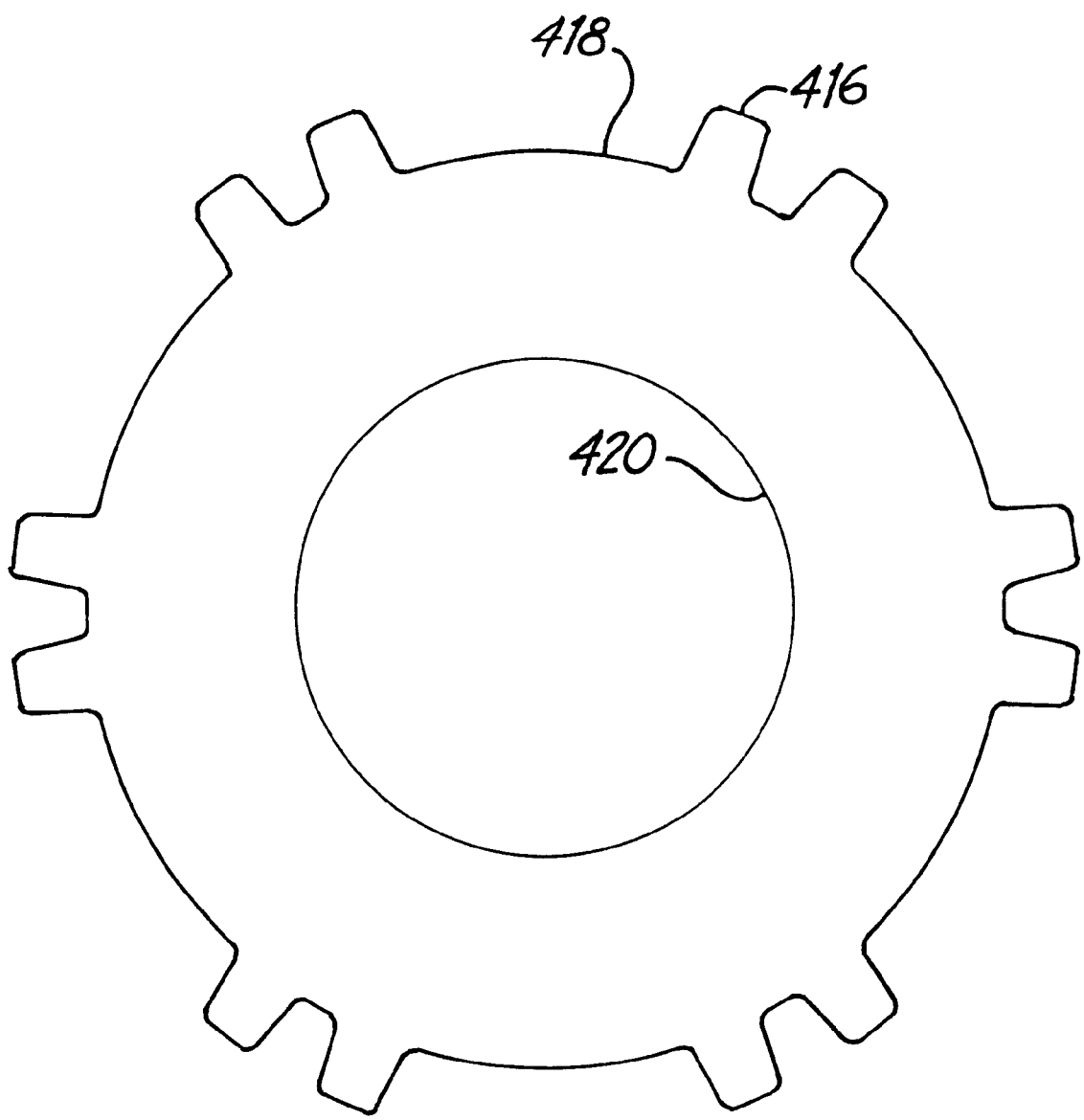
FIG. 11 is a front view of an external spline of the present invention.

The first engaging portion 408 includes an external spline 412 proximate an outer end 413 and a smooth region 414 between the first shoulder 410 and the external spline 412. The external spline 412 is a partial spline consisting of six pairs of evenly spaced apart teeth 416 as best illustrated in FIG. 11. One skilled in the art will realize that every other set of teeth 416 are machined into the first engaging portion 408 to create the partial spline although a complete spline is within the scope of the invention. Every other set of teeth 416 are machined into the first engaging portion 408 to reduce the cost and time required to manufacture the first engaging portion 408. A base diameter 418 of the external spline 412 is the same diameter as the smooth region 414.

Extending inwardly from the outer end 413 of the first engaging portion 408 is a bore 420. The bore 420 has a threaded surface and is centered about a central axis through the first engaging portion 408.

A second engaging portion 422 extends outwardly from the cylindrical portion 406 opposite the first engaging portion 408. The second engaging portion 422 is a mirror image of the first engaging portion 408 where the second engaging portion 422 has a smaller diameter than the diameter of the cylindrical portion 406 thereby defining a second shoulder 424.

The second engaging portion 422 includes an external spline 426 proximate an outer end 427 and a smooth region 428 between the second shoulder 424 and the external spline 426. The external spline 426, as best illustrated in FIG. 11, is a partial spline 412, identical to the partial spline 412 of the first engaging portion 408, consisting of six pairs of evenly spaced apart teeth 416. In this application like parts are referenced by like reference characters. One skilled in the art will realize that every other set of teeth 416 are machined into the second engaging portion 422 to create the partial spline 412. A base diameter 418 of the partial spline 426 is the same diameter as the smooth region 428.

Extending inwardly from the outer end 427 of the second engaging portion 422 is a bore (not shown). The bore (not shown) has a threaded surface and is centered about a central axis through the second engaging portion 422. One skilled in the art will recognize that the central axis of the first and second engaging portions 408, 422 align.

Figure 9:
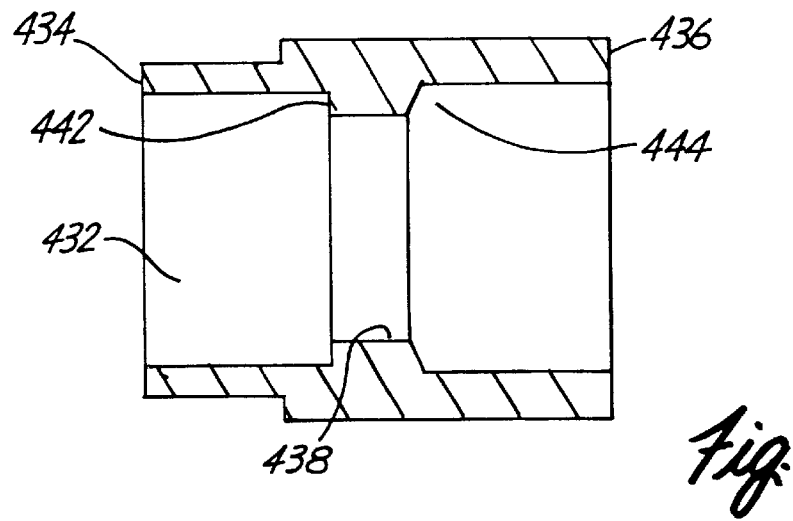
FIG. 9 is a sectional view of a dock housing of the retractor mounted embodiment of the present invention.

A first dock housing 430 cooperates with the first engaging portion 408. The first dock housing 430 is cylindrical in configuration having a bore 432 extending from a first end 434 to a second end 436, as best illustrated in FIG. 9. An internal spline 438 extends inwardly into the bore intermediate the first and second ends 434, 436.

Figure 10:
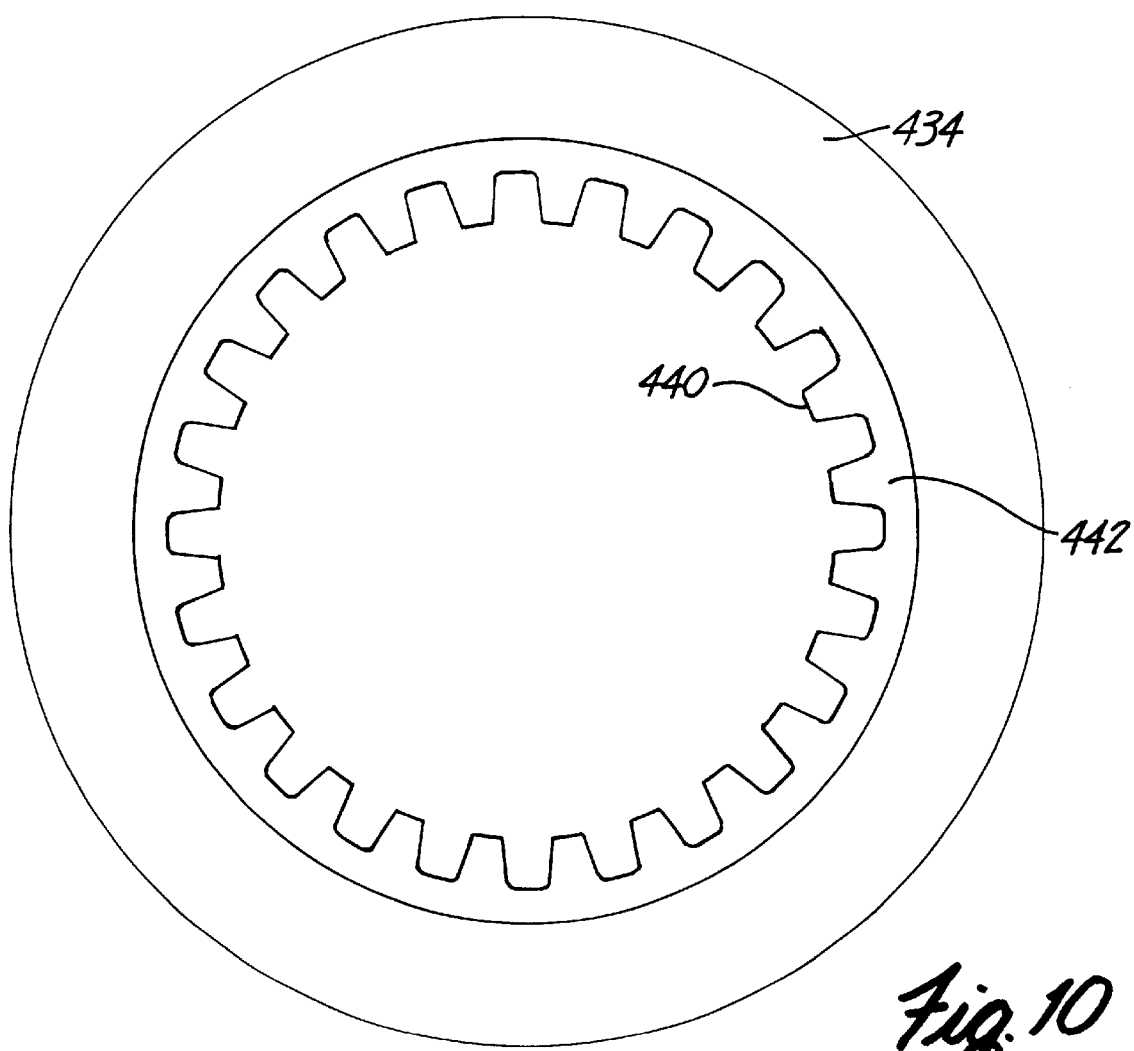
FIG. 10 is a front view of an internal spline of the present invention.

Referring to FIG. 10, the internal spline 438 is a complete spline having evenly spaced teeth 440 extending inwardly about a circumference of the bore 432. The internal spline 438 has a first end 442 and a second end 444 which define a depth of the teeth 440, as best illustrated in FIG. 9. The bore 442 proximate the first end 434 must be large enough to accommodate the external spline 412 of the first engaging portion 408.

The first dock housing 430 is positioned on the first engaging portion 408 such that the external spline 412 interacts and meshes with the internal spline 438 and thereby locks the first dock housing 430 in a selected position. The first dock 430 housing is designed such that when the internal spline 438 and the external spline 412 interact and mesh, a first end 434 of the dock housing 430 is proximate the first shoulder 410 of the cross-arm subassembly 402.

The teeth 416 of the external spline 412 mesh with the teeth 440 of the internal spline 438 to prevent rotational movement of the first dock housing 430 about the first engaging portion 408. One skilled in the art will recognize that the partial external spline 412 has enough teeth 416 cooperating with the complete internal spline 410 to distribute forces applied to a support arm 448 to prevent the teeth 416, 440 of the splines 412, 438, respectively, from sheering off.

Referring to FIG. 8, a compression spring 450 is disposed about a shoulder bolt 452. The shoulder bolt 452 has a threaded region 454, a shoulder region 456 having a larger diameter than the threaded region 454 and a head 458 having a larger diameter than the shoulder region 456. The compression spring 450 is disposed about the shoulder region 456. The shoulder bolt 452 is inserted into the bore 432 from the second end 436 of the dock housing 430.

An Allen wrench (not shown) engages a hexagon cross-sectional recess 460 in the head 458. The Allen wrench is rotated to threadably engage the threaded region 454 with the threaded bore 420 in the first engaging portion 408 until an end of the shoulder region 456 of the bolt 452 is adjacent to the outer end 413 of the first engaging portion 408. When the end of the shoulder region 456 is adjacent to the outer end 413 of the first engaging portion 408, the shoulder bolt 452 is secured into a selected position by the threadable engagement. When the shoulder bolt 452 is secured into the selected position, the first dock housing 430 is slidable about the shoulder region 456, the shoulder region 456 having substantially the same diameter as the smooth region 414 of the first engaging portion 408.

An end of the compression spring 450 contacts the second end 444 of the internal spline 430 within the first dock housing 430. Another end of the compression spring 450 contacts the head 458 of the shoulder bolt 452.

The first dock housing 430 is repositioned on the first engaging portion 408 by applying a force to the dock housing 430. The first dock housing 430 is forced away from the outer end 413 of the first engaging portion 408 such that the internal spline 438 disengages the external spline 412. When the internal spline 438 disengages the external spline 412, the first dock housing 430 can be rotated 360 degrees about the first engaging portion 408 such that the first dock housing 430 is manipulated into a desired position.

When the force is applied to the dock housing 430 which disengages the internal spline 438 from the external spline 412, the compression spring 450 is compressed between the second end 444 of the internal spline 438 and the head 458 of the shoulder bolt 452. Removing the force from the dock housing 430 after the dock housing 430 has been repositioned allows the compression spring 450 to force the dock housing 430 toward the shoulder 410 of the cross arm subassembly 402. When the dock housing 430 is forced towards the shoulder 410 of the cross arm subassembly 402, the internal spline 438 engages the external spline 412 and fixes the first dock housing 430 in the selected position. One skilled in the art will realize that the dock housing 430 can be easily and quickly repositioned by grabbing the dock housing 430, pulling the dock housing 430 away from the engaging portion 408, rotating the dock housing 430 into a desired position and releasing the dock housing 430 at which time the compression spring 450 re-engages the internal and external splines 438, 412, respectively. The meshed splines 438, 412 fix the dock housing 430 in a desired position by preventing rotation of the dock housing 430 about the first engaging portion 408.

A first wing 462 and a second wing 464 extend outwardly from a second end 466 of the first dock housing 430 in an orthogonal relationship to a central axis of the bore 432. The first and second wings 462, 464 have first and second recesses 466, 468 which engage first and second portions 470, 472, respectively, of a docking member 474. Preferably the first portion 470 is welded to the first wing 462 within the first recess 466 and the second portion 472 is welded to the second wing 464 within the second recess 468.

The docking member 474 is substantially rectangular in configuration and has a rectangular channel 476 defined therein. Within a top and a bottom member 475, 477 are sets of aligned through holes 478.

A pair of slots 480 extend through the top member of the docking member 474. The slots 480 define a flexible portion 482, a portion of which extends into the rectangular channel 476, the slots 482 giving the portion 482 flexibility.

Referring to FIG. 7, a first support arm 448 having a rectangular cross section is inserted into the rectangular channel 476 of the first docking member 474. The support arm 448 is preferably ¼" thick. The flexible portion 482 engages the first support arm 448 thereby creating a frictional engagement of the support arm 448 to the bottom member 477 and the flexible portion 482 of the docking member 474. The frictional engagement retains the first support arm 448 within the first docking member 474. The first support arm 448 can be removed from the docking member 474 by overcoming the frictional engagement.

The first support arm 448 includes a plurality of spaced apart apertures 484 along a span of the support arm 448. The apertures 484 proximate a first end 486 of the support arm 448 are aligned with the through holes 478 within the docking member 474 such that a pin (not shown) can be inserted through the aligned apertures 478, 484 and retain the support arm 448 within the docking member 474 by an alternative means.

The support arm 448 can be any configuration as long as the support arm 448 is retained within the docking member 474, but preferably the support arm 448 is arcuate or U shaped in configuration. The arcuate configuration gives a surgeon more selection from a variety of angles to access a surgical site than a straight support member. Intermediate the first end 486 and a second end 488, the support arm 448 preferably is inclined downwardly from an end 490 of a straight portion 492 thereby giving a surgeon a selection of different heights for placing a retractor relative to a wound without repositioning the first support arm 448.

Referring to FIG. 8, the second engaging portion 422 and a second dock housing 494 are mirror images of the first dock housing 430 and the first engaging portion 408. The interaction between the second engaging portion 422 and second dock housing 494 are identical to the interaction between the first dock housing 430 and first engaging portion 408. Like members of the second dock housing 494 will be referenced with like reference characters as the first dock housing 430.

The second dock housing 494 cooperates with the second engaging portion 422. The second dock housing 494 is cylindrical in configuration having a bore 432 extending from a first end 434 to a second end 436, as best illustrated in FIG. 9. The bore 432 includes an internal spline 438 intermediate the first end 434 and the second end 436. The bore 432, proximate the first end 434, must be large enough to accommodate the external spline 426 of the second engaging portion 422.

The internal spline 438 is a complete spline having evenly spaced teeth 440 extending inwardly about a circumference of the bore 432. A depth of the teeth 440 is defined by a first surface 442 proximate the first end 434 and a second surface 444 proximate the second end 436 of the second dock housing 494. The second dock housing 494 is positioned on the second engaging portion 422 such that the external spline 426 interacts and meshes with the internal spline 438 thereby locking the second dock housing 494 in a selected position. The second dock housing 494 is designed such that when the internal and external splines 438, 426 interact and mesh, the first end 434 of the second dock housing 494 is proximate the second shoulder 424 of the cross arm sub-assembly 402.

The teeth 416 of the external spline 426 mesh with the teeth 440 of the internal spline 438 to prevent rotational movement of the second dock housing 494 about the second engaging portion 422. One skilled in the art will recognize that the partial external spline 426 has enough teeth 416 cooperating with the complete internal spline 440 to distribute forces applied to a second support arm 448 to prevent the teeth 416, 440 of the splines 426, 438 from shearing off.

A compression spring 500 is disposed about a shoulder bolt 502. The shoulder bolt is the same construction and size as the first shoulder bolt 452 and those portions will be given the same reference characters. The shoulder bolt 502 has a threaded region 454, a shoulder region 456 having a larger diameter than the threaded region 454 and a head 458 having a larger diameter than the shoulder region 456. The diameter of the shoulder region 456 is substantially the same diameter as the smooth portion 428 of the second engaging portion 422. The compression spring 500 is disposed about the shoulder region 456. The bolt 502 is inserted into the bore 432 from the second end 436 of the dock housing 494.

An Allen wrench (not shown) engages a hexagon cross-sectional recess 460 within the head 458 of the shoulder bolt 452. The Allen wrench is used to threadably engage the threaded region 452 with the threaded bore (not shown) in the second engaging portion 422 until the shoulder portion 456 of the bolt 502 is adjacent to the outer end 427 of the second engaging portion 422. When the shoulder portion 456 is adjacent to the outer end 427 of the second engaging portion 422, the shoulder bolt 502 is secured into a selected position by the threadable engagement. When the shoulder bolt 502 is secured into the selected position, the second dock housing 494 is slidable about the shoulder region 456. The shoulder region 456 has the same diameter as the smooth portion 428 of the second engaging portion 422.

An end of the compression spring 500 contacts a second surface 444 of the internal spline 438 within the second dock housing 494. Another end of the compression spring 500 contacts the head 458 of the bolt 502.

The second dock housing 494 is repositioned on the second engaging portion 422 by applying a force to the dock housing 494. The second dock housing 494 is moved away from the second shoulder 424 of the cross arm subassembly 402 such that the internal spline 438 disengages the external spline 426. When the internal spline 438 disengages the external spline 426, the second dock housing 494 can be rotated 360 degrees about the second engaging portion 422 allowing the second dock housing 494 to be positioned into a desired position.

When the force is applied to the second dock housing 494 such that the internal spline 438 is disengaged from the external spline 426, the compression spring 506 is compressed between the second surface 444 of the internal spline 438 and the head 458 of the shoulder bolt 502. Removing the force from the second dock housing 494 after being repositioned allows the compression spring 500 to force the second dock housing 494 toward the second shoulder 424 of the cross arm sub-assembly 402. When the second dock housing 444 moves toward the second shoulder 424, the internal spline 438 engages the external spline 426 and fixes the second dock housing 494 in the selected position. One skilled in the art will realize that the second dock housing 494 can be easily and quickly repositioned by grabbing the second dock housing 494, pulling the second dock housing 494 away from the second engaging portion 422, rotating the second dock housing 494 about the second engaging portion 422 and into a desired position and releasing the second dock housing 494 at which time the spring 500 re-engages the internal and external splines 438, 426, respectively.

A first and second wing 462, 464 extend outwardly from the second end 436 of the second dock housing 494 in an orthogonal relationship to a central axis of the bore 432. The first and second wings 462, 464 have recesses 466, 468 which engage first and second portions 470, 472, respectively, of a docking member 474. The first portion 470 is welded to the first wing 462 within the first recess 466. The second portion 472 is welded to the second wing 464 within the second recess 468. Welding the first and the second portions 470, 472 to the first and second wings 464, 466 fixedly attaches the docking member 474 to the second dock housing 494.

The docking member 474 is substantially rectangular in configuration and has a rectangular channel 476 defined therein. Within a top member 475 and a bottom member 477 are sets of aligned through holes 478.

A pair of slots 480 extend through the top member 475 of the docking member 474. The slots 480 define a flexible portion 482, a portion of which extends into the rectangular channel 476, the slots 480 giving the portion 482 flexibility.

Referring to FIG. 7, a second support arm 498 having a rectangular cross section is inserted into the rectangular channel 476 of the second docking member 474. The second support arm 498 is preferably ¼" thick. The flexible member 482 engages the second support arm 498 thereby creating a frictional engagement of the second support arm 498 to the bottom member 477 and the flexible member 482 of the docking member 474. The frictional engagement retains the second support arm 498 within the second docking member. The second support arm 498 can be removed from the docking member 474 by overcoming the frictional engagement.

The second support arm 498 includes a plurality of spaced apart apertures 484 along a span of the support arm 498. The apertures 484 proximate a first end 504 of the second support arm 498 can be aligned with the through holes 478 within the docking member 474 such that a pin (not shown) can be inserted through the aligned apertures 478, 484 and thereby retain the support arm 498 within the docking member 474 by an alternative means.

The second support arm 498 can be any configuration as long as the support arm 498 is retained within the docking member 474, but preferably the support arm 498 is arcuate or U shaped in configuration. The arcuate configuration gives a surgeon more angles to access a surgical site than a straight support member.

Additionally, intermediate the first end 504 and a second end 506, the second support arm 498 preferably angles downwardly from a flat portion 508 thereby giving a surgeon different heights for placing a retractor relative to a wound without repositioning the second support arm 498.

The first support arm 448 is positionable independent of the second support arm 498. Similarly, the second support arm 498 is positionable independent of the first support arm 448. The ability to position the first and second support arms 448, 498 independent of each other allows a surgeon to customize the positions of the retractor support arms 448, 498 for different surgical procedures and different sized patients.

In preparation for a hip replacement surgery, the height of retractor support apparatus (not shown) is adjusted by clamping the support member 404 in a selected position on the retractor support apparatus. With the height of the support member 404 fixed, the first and second support arms 448, 498 are independently positioned to provide a surgeon the desired access to a hip joint.

To begin the surgical procedure, an incision is made into the flesh of the patient. Retractor blades which are secured to either the first or second support arms 448, 498 retract the flesh from the incision joint thereby exposing the hip joint. With the hip joint exposed, the acetabulum, the femoral head and a trunk portion of the femur are viewable through the retracted incision.

In the embodiment 400, different retractor blades 510, 512 are used to retract the femoral head from the acetabulum and to elevate the femur from the acetabulum, as best illustrated in FIG. 7. Retractor mechanisms 514 maneuver and manipulate the different blades 510, 512. The retractor mechanisms 514 are identical and only one will be described herein.

The retractor mechanism 514 is securely positioned on either the first or second support arm 448, 498 by a cooperation of a pin 516 extending downwardly from a bottom surface 518 of a gearbox assembly 520 with an aperture 484 within the support arm 448, 498. The pin 516 is in a perpendicular relationship with the bottom surface 518 and extends through a thickness of the first or second support arm 448, 498. Preferably, the thickness of the support arm 448, 498 is ¼" and the pin 516 is ¾" in length. An end of the pin 516 extends ½ inch below the bottom surface of the support arm 448, 498. The excess length of the pin 516 prevents the retractor mechanism 514 from rotating off of the support arm 448, 498 when a force is applied to the retractor blade 510, 512. The only method of removing the retractor mechanism 514 from the support arm 448, 498 is to lift the gearbox assembly 520 away from a top surface of the support arm 448, 498 until the pin 516 disengages the aperture 484 within the support arm 448, 498. While the pin 516 is disposed within the aperture 484, the retractor mechanism 514 pivots about the pin 516.

The gearbox assembly 520 includes a gearbox 522 casing attached to an outer casing 524. The outer casing 524 is preferably U shaped and includes the bottom surface 518 to which the pin 516 is attached, a top surface 528 and a first side surface 526. The gearbox casing 528 includes first and second shoulders 530, 532 which contact a first end 536 and a second end 538 of the outer casing 524. The shoulders 530, 532 are designed such that each shoulder 530, 532 is even with the top and bottom surfaces 528, 518 when the gearbox casing 528 engages the outer casing 526.

The gearbox casing 528 extends within the outer casing 526 such that a first surface 540 of the gearbox casing 528 and the top surface 529, the bottom surface 518 and the first side wall 526 define a retractor handle bore 542. The retractor handle bore 542 is preferably substantially rectangular in configuration, although other cross-sectional configurations may be used. The retractor handle bore 542 is positioned proximate a second side 560 of the gearbox assembly 520.

A channel 548 is disposed along a length of the first surface 540 of the engaging member. A pawl retaining cavity 550 is machined into the channel 548 proximate the second end 546 of the gearbox assembly 520. The pawl retaining cavity 550 extends to an outer surface of the gearbox cavity 528.

A gear bore 564 is positioned proximate a first side 562 and a first end 544 of the gearbox assembly 520. The gear bore 564 is in a substantially orthogonal relationship with the retractor handle bore 542. The gear bore 564 is in communication with the retractor handle bore 542.

A pawl 566 is inserted into the pawl retaining cavity 550 and retained within the cavity 550 by a cooperation of a pin 568 being inserted into an aperture 570 within the top surface 529, a bore (not shown) which extends into the pawl retaining cavity 550 and a bore 572 through the pawl 566 which is aligned with the bore (not shown) in the gearbox casing 528. Additionally, a bore (not shown) may continue through the pawl retaining cavity 550 to secure an end of the pin 568 within a non-moving part. The pin 568 has an engaging portion 574 proximate a head 516 which creates a frictional engagement of the pin 568 with the bore (not shown) within the gearbox casing 528, thereby retaining the pin 568 within the gearbox assembly 520 and the pawl 566 within the pawl retaining cavity 550.

A retractor handle 580 is disposed through the retractor handle bore 542. The retractor handle 580 is preferably a three sided channel which cooperates with the rectangular retractor handle bore 542. Extending from a first side 582 of the retractor handle 580 is a rack (not shown) of a rack and pinion system (not shown). When the retractor handle 580 is disposed within the retractor handle bore 542, the rack (not shown) extends within the channel 548 of the retractor handle bore 542.

A gear pin 590 is inserted into the gear bore 564 from the top surface 529 of the outer casing 524. A gear 592 having pinions 594 is disposed annularly around a circumference of the gear pin 590. The gear 592 is disposed within the gear bore 564 such that the pinions 594 extend into the channel 548 and engage grooves which define the rack (not shown). The gear pin 590 has a bore (not shown) extending from an end 596 which is aligned about a central axis of the gear pin 590. A retaining pin 598 is inserted through an aperture (not shown) within the bottom surface 518 of the outer casing 524 aligned with the bore (not shown) within the gear pin 590 when the gear pin 590 is within the gear bore 564. The retaining pin 598 has an engaging portion 600 with a slightly larger diameter than the pin 598 which secures the pin 598 within the bore (not shown) of the gear pin 590, thereby securing the gear pin 590 within the gear bore 564.

A length of the rack (not shown) determines the maximum distance that the retractor handle 580 can be moved through the retractor bore 542 by the rack and pinion system (not shown). The surgeon is easily able to manipulate the position of the retractor blade 510, 512 by rotating the gear pin 590 which in turn rotates the pinions 594 of the gear 592. The interaction of the rotating pinions 594 with the rack (not shown) causes the retractor handle 580 to move longitudinally with respect to the retractor handle bore 542 thereby allowing the surgeon to move the retractor blade 510, 512 into a desired position.

The pawl 572, which is pivotally attached to the gearbox casing 528 by the pin 568, includes a notch 573 proximate a first end 605. The notch 573 includes a substantially right corner which engages the pinions 594 of the gear 592 such that the gear pin 590 cannot be rotated counter clockwise without first displacing the notch 573 from the pinion 594 of the gear 592. The pawl 566 is biased to engage the notch 573 with the pinions 594 by a compression spring 602 engaging a shoulder 604. The spring 602 biases a second end 606 toward an outer edge of the gearbox casing 528 such that the second end 606 extends past the edge of the gear box casing 528. While the second end 606 of the pawl 566 is biased toward the edge, the first end 605 is biased toward the pinions 594. The pawl 566 prevents accidental movement of the retractor handle 580 when the rack and pinion system (not shown) applies a force to the femur to either dislocate the femoral head from the acetabulum or to elevate the femur. A length of a surface 608 proximate the second end 606 the pawl 566 prevents the second end 606 from engaging the grooves defining the rack (not shown).

Figure 12:
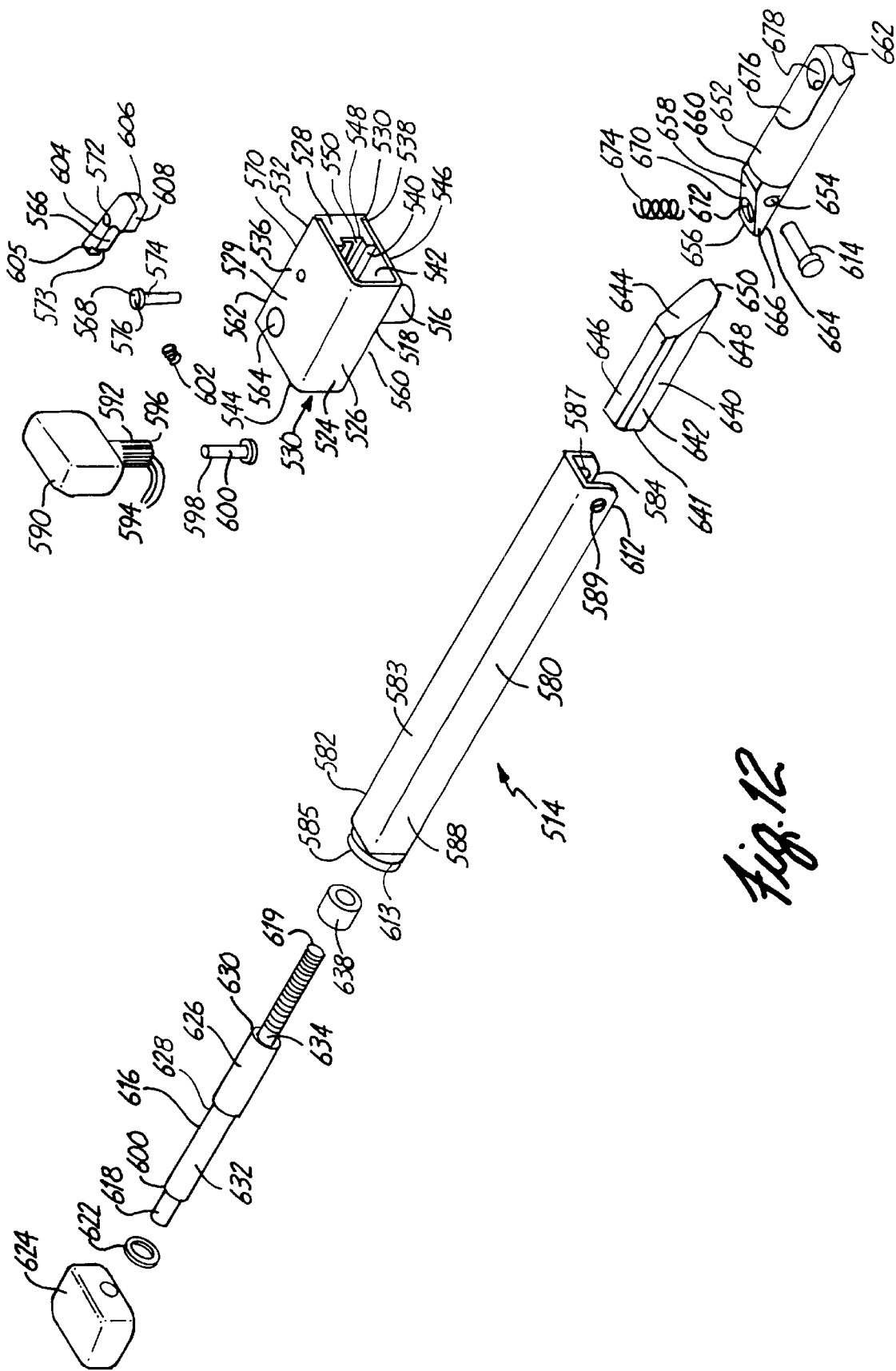
FIG. 12 is an exploded perspective view of the retractor mechanism of the present invention.

Referring to FIG. 7, an articulated joint 610 allows the retractor blade 510, 512 to be raised or lowered relative to a blade end 512 of the retractor handle 580 by a pivot pin 614. Referring back to FIG. 12, the retractor handle 580 has a rectangular channel 584 disposed through a length of the retractor handle 580 extending from the blade end 612 to a handle end 613.

A push rod 616 extends through the length of the channel 584 within the retractor handle 580. A first end 618 of the push rod 616 is disposed through an aperture 585 at the handle end 613 of the retractor handle 580. A first shoulder 620 proximate the first end 618 contacts the aperture 585, thereby fixing the push rod 616 in a selected position with respect to the retractor handle 612 while allowing the push rod 616 to be rotated. A washer 622 is disposed over the first end 618 of the push rod 616 and a knob 624 is fixedly attached the first end 618 of the push rod 616. The washer 622 prevents the handle end 613 of the retractor handle 580 from goring a surface of the knob 624 and binding the knob 624 to the handle end 613 of the retractor handle 580.

Intermediate the first end 618 and a second end 619 of the push rod 616 is a center portion 626 defining a second shoulder 628 and a third shoulder 630. The center portion 626 has a larger diameter than the diameter of portions 632, 634 adjacent to the center portion 626. The differences in the diameters define the second and third shoulders 628, 630. A spacer 638 is disposed over a second end 619 of the push rod 610. The second end 619 of the push rod 616 is threaded and threadably engages a threaded bore (not shown) within a first end 641 of a first wedge 640.

The first wedge 640 is substantially rectangular in cross section proximate the first end 641. A rectangular cross sectional portion 642 of the first wedge 640 cooperates with the rectangular channel 584 within the retractor handle 580 which prevents the first wedge 640 from rotating within the rectangular channel 584. Because the first wedge 640 does not rotate when the push rod 616 is rotated, the threadable engagement of the push rod 616 with the bore (not shown) within the first wedge 640 causes the first wedge 640 to move relative to the second end 619 of the push rod 616 when the push rod 616 is rotated. A first wedge surface 644 is defined by a flat surface extending from a top surface 646 to an edge at the bottom surface 648 at a second end 650.

A mounting member 652 has a bore 654 which aligns with first and second apertures 587, 589 within the first side 582 and a second side 588, respectively of the retractor handle 580. The pivot pin 614 is inserted through the first aperture 587, the through bore 654 and the second aperture 589 thereby pivotally attaching the mounting member 652 to the retractor handle 580.

Proximate a first end 656 of the mounting member 652 is a second wedge surface 658. The wedge surface 658 extends from a top surface 660 intermediate the first end 656 and a second end 662 to a bottom surface 664 proximate the first end 656. An angled surface 666 extends upwardly at a slat from the bottom surface 664 toward the first end 656 such that the first end 656 of the mounting member 652 is an edge above the bottom surface 664.

As the push rod 616 is rotated, the pointed end 650 of the first wedge surface 644 engages the angled surface 666 of the mounting member 652. Further movement of the first wedge surface 644 toward the mounting member 652 causes the mounting member 652 to pivot about the pin 614 while the angled surface 666 travels up the first wedge surface 644.

The second wedge surface 658 has a circular recess 670 which cooperates with a compression spring 674. An end of the compression spring 674 rests on a substantially flat, bottom surface 672 of the circular recess 670. Another end of the compression spring 634 is positioned against an inner surface of a top member 583 of the retractor handle 580.

As the angled surface 666 travels up the first wedge surface 644, the compression spring 674 compresses which biases the angled surface 666 to travel down the first wedge surface 644 as the first wedge 640 is manipulated away from the mounting member 652. One skilled in the art will realize that the second wedge surface 658 allows for greater pivotal movement of the mounting member 652 because the first end 656 of the mounting member 652 will not contact the top surface 583 of the retractor handle 580 until the second wedge surface 658 contacts the top surface 583. One skilled in the art will also recognize that because the mounting member 652 is pivotally attached to the retractor handle 580 between the first end 656 and a second end 662 that as the first end 656 is raised the second end 662 is lowered and vice versa.

Referring to FIG. 13, a cylindrical portion 676 extends from the mounting member 652. A through bore 678 is disposed through the cylindrical portion 676 proximate the second end 662 of the mounting member 652. A shoulder 680 is defined proximate an end of the cylindrical portion 676.

A plug 682 having a bore 684 extending from a first end 686 to a second end 688 is disposed over the cylindrical portion 676 of the mounting member 652 until the first end 686 is adjacent to the shoulder 680. With the first end 686 of the plug 682 adjacent to the shoulder 680, a first slot 690 within a first side surface 696 of a rectangular body 697 and a second slot 692 within a second side surface 698 of the rectangular body 697 are aligned with the through bore 678 within the cylindrical member 676.

A pin 700 is inserted through the first slot 690, the through bore 678 and the second slot 692. An end of the pin 700 is substantially even with an outer surface of the first side surface 696 and another end of the pin 700 is substantially even with an outer surface of the second side surface 698. Neither end of the pin 700 extends past the outer surfaces of the first and second sides 696, 698. The slots 690, 692 are wider than the diameter of the pin 700 allowing the plug 682 to partially rotate about the cylindrical portion 676 until the pin 700 contacts either surface of the slots 690, 692. Preferably, the plug 682 rotates 10 to 20 degrees about the cylindrical portion 676.

A retractor engaging member 702 having a rectangular bore (not shown) extending from a first end 704 cooperates with the rectangular body 697 of the plug 682. The cooperation of the rectangular body 697 with the rectangular bore (not shown) prevents rotation of the retractor engaging member 702 about the plug 682. The retractor engaging member 702 is positioned on the plug 682 until the first end 704 of the retractor engaging member 702 contacts a shoulder 683 about the plug 682. The outer surface around a perimeter of the shoulder 683 is even with the rectangular outer surface of the retractor engaging member 702.

Proximate a second end 706 of the retractor engaging member 702 is a through bore 708. Extending from an end of a retractor blade 510, 512 is a cylindrical member 710 which cooperates with the through bore 708. The cooperation of the cylindrical member 710 with the through bore 708 allows the retractor blade 510, 512 to rotate about the cylindrical member 710.

Referring to FIG. 7, the present invention includes two different blades, a femur retractor blade 510 and a femur elevator blade 512, each of which are attachable to the retractor mechanism 514 by the cooperation of the cylindrical portion 710 attached to the blade 510, 512 with the through bore 708 in the retractor blade engaging member 708. The femur retractor blade 510 is hook shaped having a curved end 511. The femur elevator retractor blade 512 is arcuate in configuration having an upwardly curved end 515. A slot 517 is substantially centrally located within the upwardly curved end 515.

Each retractor blade 510, 512 is used for different purposes during a hip replacement surgery. Prior to making an incision, the first and second support arms 448, 498 are adjusted to a position desired by the surgeon. After an incision has been made, the flesh is retracted to expose the hip joint by a standard flat retractor blade which is well known in the art. After exposing the hip joint, the retracting mechanism 514, to which the femur retractor blade 510 is attached, is positioned in a desired location by inserting the pin 516 extending from a bottom surface 518 of the gearbox assembly 520 into an aperture 484 within either the first or second support arms 448, 498.

After positioning the retracting mechanism 514 in the desired aperture 484, the gear pin 590 is manipulated to position the hook end 511 of the femur retractor blade 510 above the femoral head and the femoral trunk. Rotating the gear pin 590 causes the pinions 594 of the gear 592 to engage the rack (not shown) attached to the retractor handle 580 which causes the retractor handle 580 and the retractor blade 510 to move toward the hip joint. Once the femur retractor blade 510 is positioned above the femoral head or the femoral trunk, the height of the retractor blade 510 is adjusted.

The height of the femur retractor blade 510 is adjusted by rotating the knob 624 proximate the handle end 585 of the retractor handle 580. Rotating the knob 624 causes the first wedge 644 to engage the angled surface 666 of the mounting member 652 causing the first end 656 of the mounting member 552 to rise up the wedge 644. As the first end 656 rises up the first wedge 644, the second end 662 of the mounting member 552 pivots downward about the pin 614. The second end 662 is pivoted downward until the hook end 511 of the femur retractor blade 510 is positioned about the femoral trunk. The position of the hook end 571 can be slightly adjusted by rotating the retractor engaging member 708 about the cylindrical portion 676 of the mounting member 652.

With the hook end 571 of the femur retractor in the desired location the gear pin 590 is rotated in an opposite direction thereby causing the rack and pinion system (not shown) to move the retractor handle 580 and the retractor blade 510 away from the hipjoint. As the retractor blade 510 is moved away from the hip joint by the rack and pinion system (not shown), a force is applied to the hip joint until the femoral head is dislocated from the acetabulum. The retractor support apparatus (not shown) provides the support required to prevent movement of the retractor 574 and the support arm 448, 498. The pawl 566 engages the pinions 594 of the gears 592, preventing the retractor handle 580 from inadvertently moving toward the hip joint and releasing the force applied by the femur retractor blade 510. Additionally, the pawl 566 allows the surgeon to rest if needed during the dislocation process without having to reapply the force already applied to the femur.

Once the femoral head is dislocated from the acetabulum, the rotation of the gear pin 590 is reversed to disengage the femur retractor blade 510 from the femur. Once the femur retractor blade 510 disengages the femur, the retractor blade 510 is raised by reversing the rotation of the knob 624 thereby maneuvering the first wedge 644 away from the retractor end 587 of the handle 580 which allows the compression spring 674 to force the first end 656 of the mounting member 652 downward thereby raising the second end 662 along with the retractor blade 510. With the retractor blade 510 disengaged from the femur, the retractor mechanism 514 including the femur retractor blade 510 can be removed from the surgical site by disengaging the pin 516 from the aperture 484 within the support arm 448, 498 by lifting the retractor mechanism 514 upward.

The use of the mechanically adjustable retractor mechanism 514 allows the femoral head to be dislocated from the acetabulum using a minimum amount of force and minimum amount of movement as necessary to dislocate the hip joint. Using only the required force and minimizing movement reduces the amount of trauma to the patient and reduce the amount of time required to recover.

The surgeon may need to elevate and move the femur and the femoral head to gain access to the acetabulum. The femur elevating retractor blade 512 is used to move the femur and the femoral head. The pin 516 of another retractor mechanism 514 is inserted into a desired aperture 484 within a support arm 448, 498. The femur elevating retractor blade 512 is positioned proximate the femoral head by manipulating the gear pin 590 and the knob 624 to adust the position and height of the femur elevating blade 512. The slot 517 is positioned below the femoral trunk such that the femoral head is secured within an arcuate surface 519 of the femur elevating blade 512. The knob 624 is rotated to raise the femoral head by manipulating the first wedge 644 away from the joint thereby allowing the compression spring 674 to lower the first end 656 of the mounting mechanism 652 and raise the second end 662 along with the femur elevating blade 512.

Once the femoral head has been raised, the femoral head is displaced from the acetabulum by rotating the gear pin 590 and engaging the rack and pinion system (not shown) to give the surgeon the required access to the acetabulum. The weight of the dislocated leg secures the pin 516 within aperture 484 within the support arm 448, 498. The retractor support apparatus 402 provides a support which counteracts the weight of the leg upon the retractor blade 512 such that the retractor blade 512 has the support and stability to safely engage and maneuver the femoral head. The pawl 566 prevents accidental repositioning of the femur when a force created by the rack and pinion system (not shown) is released by the surgeon. Additionally the use of the femur elevating retractor blade 512 along with the retractor mechanism 514 to move and raise the femur reduces the number of surgeons required to perform the surgical procedure because a surgeon is not needed to provide a force to displace the femur from the acetabulum.

Once the procedure has been performed on the acetabulum, the rotation of the gear pin 590 is reversed to engage the rack and pinion system (not shown) which positions the femoral head directly above the acetabulum. With the femoral head above the acetabulum, the femur elevating blade 512 is lowered by reversing the rotation of the knob 624 until the femoral head is adjacent to the acetabulum. The femur elevating blade 512 is manipulated to disengage the femoral head. Once the femur elevating blade 512 disengages the femoral head, the surgeon raises the pin 516 from the aperture 484 thereby removing the retractor mechanism 514 from the surgical site.

With the femoral head adjacent to the acetabulum, the surgeon forces the femoral head into the surgically repaired acetabulum. The use of mechanical positioning devices 514 for the femur elevating blade 512 allows the acetabulum to be accessible while limiting the movement of the femur and thereby reducing the amount of trauma to the patient which should allow the patient to recovery more quicky.

Although the present invention has been described with reference to preferred embodiments, workers skilled in the art will recognize that changes may be made in form and detail without departing from the spirit and scope of the invention.

What is claimed is:

1. A method for performing hip surgery using at least one support arm attached to a retractor support apparatus comprising:
   incising a patient to expose a hip joint, the hip joint including an acetabulum, a femur, a femoral head and a femoral trunk connecting the femur to the femoral head;
   mounting a femur retractor on one of the support arms;
   positioning the femur retractor about the femur;
   dislocating the femoral head from the acetabulum with the femur retractor;
   disengaging the femur retractor from the femur;
   positioning a femur elevating retractor on one of the support arms;
   engaging the femur with the femur elevating retractor; and
   adjusting the femoral head with the femur elevating retractor thereby making the acetabulum accessible.

2. The method of claim 1 wherein two support arms are independently positionable with respect to the hip joint.

3. The method of claim 2 wherein each support arm includes a plurality of apertures along a length of each arm.

4. The method of claim 3 wherein a pin extending from the femur elevating retractor cooperates with the surface defining the aperture to secure the femur elevating retractor to the support arm.

5. The method of claim 4 wherein the pin of the femur elevating retractor disengages the surface defining the aperture thereby being removed from the surgical site.

6. The method of claim 2 wherein each support arm has an arcuate configuration.

7. The method of claim 2 wherein a pin extending from the femur retractor cooperates with an aperture within a support arm to retain the femur retractor on the support arm.

8. The method of claim 7 wherein the femur retractor is removed from the surgical site by disengaging the pin from the surface defining the aperture within the support arm.

9. The method of claim 8 wherein the femur elevating retractor repositions the femoral head proximate the acetabulum after repairing the acetabulum.

10. The method of claim 9 wherein the rack and pinion system repositions the femoral head proximate the acetabulum.

11. The method of claim 9 wherein the femur elevating blade is pivotally lowered thereby disengaging the blade from the femoral head.

12. The method of claim 2 wherein pressure is applied to the femoral head thereby positioning the femoral head within the acetabulum.

13. The method of claim 1 wherein the femur retractor comprises a hook shaped blade.

14. The method of claim 13 wherein a longitudinal position of the hook shaped blade is adjustable relative to the hip joint.

15. The method of claim 14 wherein the longitudinal position of the hook shaped blade adjusts by manipulating a rack and pinion system.

16. The method of claim 15 wherein the rack and pinion system comprises a gear having a plurality of pinions around a circumference of the gear that engages a rack attached to a retractor handle.

17. The method of claim 13 wherein a height of the hook shaped blade is adjustable.

18. The method of claim 17 wherein the height of the hook shaped blade mechanically adjusts such that the hook shaped blade disposes about the femur.

19. The method of claim 18 wherein the rack and pinion system retracts the hook shaped blade such that the hook shape blade applies a force to the femur resulting in the femoral head dislocating from the acetabulum.

20. The method of claim 19 wherein manipulation of the rack and pinion system detaches the hook shaped retractor blade from the femur.

21. The method of claim 17 wherein the hook shaped blade pivotally attaches to the retractor handle.

22. The method of claim 1 wherein the femur elevating retractor comprises a retractor blade having an upwardly curved end.

23. The method of claim 22 wherein the upwardly curved end includes a slot disposed therein.

24. The method of claim 23 wherein slot engages a bottom surface of the femoral trunk and the femoral head engages the curved portion.

25. The method of claim 24 wherein the femur elevating retractor raises the femur making the acetabulum accessible.

26. The method of claim 25 wherein the femur elevating retractor displaces the femoral head longitudinally from the acetabulum.

27. The method of claim 26 wherein a rack and pinion system of the femur elevating retractor displaces the femoral head from the acetabulum.

28. A method for performing hip surgery using a table mounted retractor wherein the surgery includes incising a patient so as to expose the hip, the hip including an acetabulum, a femur, and a femoral head attached to the femur and seated in the acetabulum, creating a surgical site, the surgical method comprising:
   mounting a support structure to a side rail on an operating table;
   clamping a hip retractor to the support structure, the hip retractor comprising a tubular retractor arm, a push rod extending through the inside of the tubular retractor arm having a handle end and a blade end, an articulated joint fixed to the blade end of the tubular arm, the articulated joint having a rod end and a blade end, a retractor blade fixed to the blade end of the articulated joint, and a handle affixed to the handle end of the push rod;

extending the blade of the hip retractor over the hip by rotating the handle to move the push rod through the tubular retractor arm; and dislocating the femoral head from the acetabulum wherein the retractor mounted to the support structure provides a counter force opposing the tendency of the femoral head to stay seated in the acetabulum.

29. The method of claim 28, further comprising:

manipulating the femur within the surgical site, wherein the support structure provides force to hold the femur in place with respect to the surgical site.

30. The method of claim 29, wherein the retractor is extended over the femur, proximate to the femoral head.

31. The method of claim 30 and further comprising the step of:

pivoting the articulated joint and the femoral head, wherein pivoting the articulated joint manipulates the femoral head within the surgical site.

32. The method of claim 31, wherein the hip retractor further includes a rack and pinion gearing system including a rack gear disposed on the outside of the tubular retractor arm, and a pin gear engaged with the rack gear, wherein the step of dislocating the femoral head further comprises:

rotating the pin gear; and translating the tubular retractor arm away from the acetabulum.

33. The method of claim 32, wherein the support structure includes a support post, a sidebar clamp, wherein actuating the clamp immovably fixes the support post to the support, further comprising the steps of:

adjusting the position of the sidebar clamp with respect to the side bar; and actuating the clamp to fix the clamp in position.

34. The method of claim 33, wherein the support structure further includes a support arm, and a support clamp, wherein the support clamp fixes the support arm to the support post, further comprising the steps of:

adjusting the position of the support clamp with respect to the support post; and actuating the clamp to fix the clamp in position.

35. The method of claim 34, wherein adjusting the position of the sidebar clamp and the support clamp manipulates the position of the blade within the surgical site.

36. The method of claim 35, wherein the retractor blade includes, a first prong, a second prong, and a projection, and wherein the femoral head includes a ball and a trunk, wherein the step of extending the hip retractor over the hip further comprises:

disposing the trunk between the first and second prong of the retractor blade; and disposing the projection so as to supportively engage the ball.

37. A retractor assembly apparatus mounted to an operating table having a sidebar, comprising:

a support structure mounted to the sidebar;

a tubular retractor arm having a handle end and a joint end;

a rack and pinion gear assembly engaged with the tubular retractor arm;

a push rod extending through the inside of the tubular retractor arm;

an articulated joint having an arm end and a blade end, the arm end fixed to the joint end of the tubular retractor arm; and a retractor blade fixed to the blade end of the articulated joint.

38. The apparatus of claim 37, further comprising:

an angle bar, including a first bore and a second bore, wherein the first and second bores are disposed through the angle bar and are in communication;

a rack gear disposed on the tubular retractor arm, wherein the tubular retractor arm is disposed through the first bore; and a pin gear disposed through the second bore, disposed so as to engage the rack gear.

39. The apparatus of claim 38, wherein rotating the pin gear causes the tubular retractor arm to translate through the first bore.

40. The apparatus of claim 39, wherein the articulated joint further comprises:

a finger pivotably mounted to the joint having a first end and a second end;

an elongated slot extending in the first end of the finger; and a ball fixed to the push rod and slidably enveloped in the elongated slot.

41. The apparatus of claim 40, wherein extending the push rod into the articulated joint pivots the finger.

42. The apparatus of claim 41, wherein the support structure comprises:

a support post;

a sidebar clamp, wherein the sidebar clamp fixes the support post to the side rail;

a support arm; and a support clamp, wherein the support clamp fixes the support arm to the support post.

43. The apparatus of claim 42, further comprising:

a handle, wherein the handle is rotatably fixed to the handle end of the tubular retractor arm and fixably connected to the push rod, wherein rotating the handle causes the push rod to extend into the articulated joint.

44. A method of minimizing a force required to prepare a hip joint for hip surgery comprising:

incising a patient to expose the hip joint, the hip joint including an acetabulum, a femur, a femoral head and a femoral trunk connecting the femoral head to the femur, the femoral head seated in the acetabulum;

positioning a femur retractor on a support arm;

engaging the femur retractor with the femur;

applying the force to the femur with a mechanical system of the femur retractor until the femoral head dislocates from the acetabulum;

positioning a femur elevating retractor on the support arm; and raising the femoral head from the acetabulum with the femur elevating retractor.

45. The method of claim 44 wherein the mechanical system applying the force comprises a rack and pinion system.

46. The method of claim 45 wherein an articulated joint raises and lowers the femur retractor to position the femur tractor relative to the femur.

47. The method of claim 44 wherein a blade of the femur retractor has a hook shape.

48. The method of claim 44 wherein an articulated joint of the femur elevating retractor manipulates the height of the femoral head with respect to the acetabulum.

49. The method of claim 44 and further comprising longitudinally displacing the femoral head from acetabulum with a mechanical mechanism of the femur elevating retractor to minimize trauma to a leg associated with the dislocated hip joint.

50. The method of claim 49 wherein the mechanical mechanism comprises a rack and pinion system wherein a pawl prevents slippage of the rack and pinion when applying the force.

51. The method of claim 44 wherein a blade of the femur elevating retractor comprises an arcuate end having a slot disposed therein.

52. A method of reducing a number of surgical personnel required to perform a surgical procedure on a hip joint, the method comprising:

incising a patient so as to expose the hip joint, the hip joint including an acetabulum, a femoral head, a femur and a femoral trunk connecting the femur to the femoral head, the femoral head seated in the acetabulum;

positioning a femur retractor on a support;

manipulating the femur elevating retractor such that a femur elevating retracting blade engages the femur by manipulating a mechanical system of the femur retractor such that a movement of the femur retractor blade produces a minimum force required to dislocate the femoral head from the acetabulum without aid from other personnel;

position a femur elevating retractor on a support; and manipulating the femur retractor such that a blade of the femur retractor engages the femur wherein a mechanical system of the femur elevating retractor produces a force to displace and retain the femoral head a distance from the acetabulum without aid from other personnel.

53. The method of claim 52 wherein the mechanical system comprises a rack and pinion system.

54. The method of claim 53 wherein a pawl prevents an opposite inadvertent movement of the retractor blade thereby reducing the need for another person to maintain constant force on the femoral head during the dislocation procedure.

55. The method of claim 52 wherein the mechanical system of the femur elevating retractor is a rack and pinion system cooperating with a pawl.

56. The method of claim 52 wherein manipulation of an articulated joint of the femur elevating retractor raises and lowers the femoral head mechanically without requiring aid from another person.

57. The method of claim 56 wherein after completing a repair to the hip joint the rack and pinion system is manipulated to position the femoral head above the acetabulum and wherein manipulation articulated joint positions the femoral head proximate the acetabulum.

* * * * *